United States Patent
Swiston et al.

(10) Patent No.: US 10,332,638 B2
(45) Date of Patent: Jun. 25, 2019

(54) METHODS AND SYSTEMS FOR PRE-SYMPTOMATIC DETECTION OF EXPOSURE TO AN AGENT

(71) Applicant: Massachusetts Institute of Technology, Cambridge, MA (US)

(72) Inventors: Albert Joseph Swiston, Somerville, MA (US); Tejash Mukesh Patel, Acton, MA (US); Lauren Milechin, Acton, MA (US); Jack Gerald Fleischman, Groton, MA (US); William Donald Pratt, Frederick, MD (US); Anna Nichole Honko, Frederick, MD (US)

(73) Assignee: Massachusetts Institute of Technology, Cambridge, MA (US)

( * ) Notice: Subject to any disclaimer, the term of this patent is extended or adjusted under 35 U.S.C. 154(b) by 158 days.

(21) Appl. No.: 15/212,769

(22) Filed: Jul. 18, 2016

(65) Prior Publication Data

US 2017/0112379 A1    Apr. 27, 2017

Related U.S. Application Data

(60) Provisional application No. 62/193,961, filed on Jul. 17, 2015.

(51) Int. Cl.
*A61B 5/00*     (2006.01)
*G16H 50/80*    (2018.01)
(Continued)

(52) U.S. Cl.
CPC .............. *G16H 50/80* (2018.01); *A61B 5/00* (2013.01); *A61B 5/0006* (2013.01);
(Continued)

(58) Field of Classification Search
CPC ..... G06F 19/345; G06F 19/3493; A61B 5/00; A61B 5/0006; A61B 5/0008; A61B 5/02108
See application file for complete search history.

(56) References Cited

U.S. PATENT DOCUMENTS

| | | | |
|---|---|---|---|
| 2014/0235956 A1 | 8/2014 | Kalkstein et al. | |
| 2016/0070879 A1* | 3/2016 | Hatlelid | G16H 50/50 705/3 |
| 2018/0000428 A1 | 1/2018 | Swiston et al. | |

FOREIGN PATENT DOCUMENTS

| | | |
|---|---|---|
| WO | WO 2013/036677 A1 | 3/2013 |
| WO | WO 2016/040295 A1 | 3/2016 |

OTHER PUBLICATIONS

Tseng et al., "Multiple Time Series Clinical Data Processing for Classification with Merging Algorithm and Statistical Measures," IEEE Journal of Biomedical and Health Informatics, Sep. 12, 2014, pp. 1-7, XP055315104, Piscataway, NJ, USA.

(Continued)

*Primary Examiner* — Paula J Stice
(74) *Attorney, Agent, or Firm* — Wolf, Greenfield & Sacks, P.C.

(57) ABSTRACT

Systems and methods are disclosed herein for predicting whether a patient has been exposed to an agent. Physiological data is recorded from the patient during a first time interval, and one or more features are extracted from the physiological data. A plurality of classifiers is identified, wherein each classifier is trained using training data for a respective specific post-exposure time interval. For each classifier and based on a respective subset of the one or more features, a patient state classification that indicates an initial prediction of whether the patient has been exposed to the agent is determined. An indication of a prediction that the patient has been exposed to the agent is provided when a (Continued)

number of patient state classifications indicating a positive initial prediction that the patient has been exposed to the agent exceeds a first threshold.

13 Claims, 12 Drawing Sheets

(51) Int. Cl.
    *G16H 50/20*     (2018.01)
    *A61B 5/021*     (2006.01)
    *A61B 5/08*     (2006.01)

(52) U.S. Cl.
    CPC ............ *A61B 5/0008* (2013.01); *A61B 5/021* (2013.01); *A61B 5/08* (2013.01); *G16H 50/20* (2018.01)

(56) References Cited

OTHER PUBLICATIONS

International Search Report and Written Opinion for PCT/US2016/042848 dated Nov. 14, 2016.
International Preliminary Report on Patentability dated Feb. 1, 2018 for Application No. PCT/US2016/042848.
International Search Report and Written Opinion dated Aug. 11, 2017 for Application No. PCT/US2017/033393.
[No Author Listed], Questions and Answers about Ebola Hermorrhagic Fever. Center for Disease Control and Prevention. http://www.cdc.gov.ncidod/dvrd/spb/mnpages/dispages/ebola/qa.htm. Last reviewed Jul. 31, 2012. Downloaded from the Wayback Machine on Apr. 10, 2018. Aug. 2, 2012 occurrence. https://web.archive.org/web/20120802155312/http://www.cdc.gov.ncidod/dvrd/spb/mnpages/dispages/ebola/qa.htm.. 5 pages.
Ahmad et al., Continuous multi-parameter heart rate variability analysis heralds onset of sepsis in adults. PLoS One. Aug. 2009;4(8):e6642(1-10).
Banaee et al., Data mining for wearable sensors in health monitoring systems: A review of recent trends and challenges. Sensors (Basel). Dec. 17, 2013;13(12):17472-500. doi: 10.3390/s131217472.
Basak et al., KiMS: Kids' Health Monitoring System at day-care centers using wearable sensors and vocabulary-based acoustic signal processing. IEEE 13th Intl Conf on e-Health Networking, Apps, and Services. Jun. 13-15, 2011. 8 pages.
Bazett, An analysis of the time-relations of electrocardiograms. Heart. 1920;7:353-70. Republished in Ann Noninvasive Electrocardiol. History of Cardiology. Apr. 1997;2(2):177-94.
Beshuizen et al., Endotoxin and the hypothalamo-pituitary-adrenal (HPA) axis. J Endotoxin Res. 2003;9(1):3-24.
Bravi et al., Review and classification of variability analysis techniques with clinical application. BioMed Eng OnLine. Oct. 2011;10(1):90(1-27).
Breiman, Random forests. Machine Learning. 2001;45:5-32. doi: 10.1023/A:1010933404324.
Caballero et al., Lassa and Marburg viruses elicit distinct host transcriptional responses early after infection. BMC Genomics. Nov. 6, 2014;15:960(1-12). doi: 10.1186/1471-2164-15-960.
Cancio et al., Combat casualties undergoing lifesaving interventions have decreased heart rate complexity at multiple time scales. J Crit Care. Dec. 2013;28(6):1093-8. doi: 10.1016/j.jcrc.2013.08.022. Epub Oct. 17, 2013.
Caruana et al., An empirical comparison of supervised learning algorithms. Proc 23rd Intl Conf on Machine Learning (ICML). 2006. Pittsburgh, PA, USA: ACM. pp. 161-168.
Chen et al., Characteristics of heart rate variability can predict impending septic shock in emergency department patients with sepsis. Acad Emerg Med. May 2007;14(5):392-7.
Cover et al., Nearest neighbor pattern classification. IEEE Trans on Information Theory. Jan. 1967;13(1):21-7.

Dillard, A moving-window detector for binary integration. IEEE Trans on Information Theory. Jan. 1967;13(1):2-6.
Drosten et al., Rapid detection and quantification of RNA of Ebola and Marburg viruses, Lassa virus, Crimean-Congo hemorrhagic fever virus, Rift Valley fever virus, dengue virus, and yellow fever virus by real-time reverse transcription—PCR. J Clin Microbiol. Jul. 2002;40(7):2323-30.
Ek et al., Inflammatory response: Pathway across the blood-brain barrier. Nature. Mar. 22, 2001;410(6827):430-1.
Enseleit et al., Long-term continuous external electrocardiographic recording: A review. Europace. Apr. 2006;8(4):255-66. Epub Feb. 3, 2006.
Ewers et al., Natural History of Aerosol Exposure with Marburg Virus in Rhesus Macaques. Viruses. Mar. 30, 2016;8(4):87(1-16). doi: 10.3390/v8040087.
Fridericia, The duration of systole in an electrocardiogram in normal humans and in patients with heart disease. 1920. Ann Noninvasive Electrocardiol. Oct. 2003;8(4):343-51.
Funk, Prostaglandins and leukotrienes: Advances in eicosanoid biology. Science. Nov. 30, 2001;294:1871-5.
Geisbert et al., Pathogenesis of Ebola hemorrhagic fever in primate models: Evidence that hemorrhage is not a direct effect of virus-induced cytolysis of endothelial cells. Am J Pathol. Dec. 2003;163(6):2371-82.
Godin et al., Uncoupling of biological oscillators: a complementary hypothesis concerning the pathogenesis of multiple organ dysfunction syndrome. Crit Care Med. Jul. 1996;24(7):1107-16.
Goldberger et al., What is physiologic complexity and how does it change with aging and disease? Neurobiol Aging. Jan.-Feb. 2002;23(1):23-6.
Griffin et al., Toward the early diagnosis of neonatal sepsis and sepsis-like illness using novel heart rate analysis. Pediatrics. Jan. 2001;107(1):97-104.
Gupta et al., Monocyte-derived human macrophages and peripheral blood mononuclear cells infected with ebola virus secrete MIP-1alpha and TNF-alpha and inhibit poly-IC-induced IFN-alpha in vitro. Virology. May 25, 2001;284(1):20-5.
Guzzetti et al., Linear and non-linear 24 hr heart rate variability in chronic heart failure. Auton Neurosci. Dec. 28, 2000;86(1-2):114-9.
Hausdorff et al., Gait variability and basal ganglia disorders: Stride-to-stride variations of gait cycle timing in Parkinson's disease and Huntington's disease. Mov Disord. May 1998;13(3):428-37.
Hayden et al., Local and systemic cytokine responses during experimental human influenza A virus infection. Relation to symptom formation and host defense. J Clin Investig. Feb. 1, 1998;101(3):643-9.
Hensley et al., Proinflammatory response during Ebola virus infection of primate models: possible involvement of the tumor necrosis factor receptor superfamily. Immunol Lett. Mar. 1, 2002;80(3):169-79.
Jelson et al., Modulation of guinea pig intrinsic cardiac neurons by prostaglandins. Am J Physiol Regul Integr Comp Physiol. Sep. 2003;285(3):R682-9. Epub Jun. 5, 2003.
Klein et al., The cyclooxygenase-2 product prostaglandin E2 modulates cardiac contractile function in adult rat ventricular cardiomyocytes. Pharmacol Res. Feb. 2004;49(2):99-103.
Kojic et al., Are there new approaches for diagnosis, therapy guidance and outcome prediction of sepsis? World J Exp Med. May 20, 2015;5(2):50-63. doi: 10.5493/wjem.v5.i2.50.
Korach et al., Cardiac variability in critically ill adults: Influence of sepsis. Crit Care Med. Aug. 2001;29(7):1380-5.
Kortepeter et al., Basic clinical and laboratory features of filoviral hemorrhagic fever. J Infect Dis. Nov. 2011;204 Suppl 3:S810-6. doi: 10.1093/infdis/jir299.
Kowallik et al., Breath-to-breath variability correlates with apnea-hypopnea index in obstructive sleep apnea. Chest. Feb. 2001;119(2):451-9.
Ksiazek et al., Clinical virology of Ebola hemorrhagic fever (EHF): virus, virus antigen, and IgG and IgM antibody findings among EHF patients in Kikwit, Democratic Republic of the Congo, 1995. J Infect Dis. Feb. 1999;179 Suppl 1:S177-87.

(56) References Cited

OTHER PUBLICATIONS

Lake et al., Sample entropy analysis of neonatal heart rate variability. Am J Physiol Regul Integr Comp Physiol. Sep. 2002;283(3):R789-97.

Laupland, Fever in the critically ill medical patient. Crit Care Med. Jul. 2009;37(7 Suppl):S273-8. doi: 10.1097/CCM.0b013e3181aa6117.

Leroy et al., Human asymptomatic Ebola infection and strong inflammatory response. The Lancet. Jun. 24, 2000;355(9222):2210-5.

Madan et al., Social sensing for epidemiological behavior change. Proc 12th ACM Intl Conf on Ubiquitous Computing (UbiComp '10). Sep. 2010 Copenhagen, Denmark. ACM. pp. 291-300.

Martinez et al., Macrophage activation and polarization. Front Biosci. Jan. 1, 2008;13:453-61.

Pantelopoulos et al., A survey on wearable sensor-based systems for health monitoring and prognosis. IEEE Transactions on Systems, Man and Cybernetics, Part C: Applications and Reviews. Jan. 2010;40(1):1-12.

Papaioannou et al., Temperature variability analysis using wavelets and multiscale entropy in patients with systemic inflammatory response syndrome, sepsis, and septic shock. Crit Care. Mar. 2012;16:R51(1-15).

Rish, An empirical study of the naïve Bayes classifier. IJCAI 2001 Workshop on Empirical Methods in Artificial Intelligence. Jan. 2001;41-46.

Saper et al., Neural circuitry engaged by prostaglandins during the sickness syndrome. Nat Neurosci. Aug. 2012;15(8):1088-95. doi: 10.1038/nn.3159. Epub Jul. 26, 2012.

Scheff et al., Modeling physiologic variability in human endotoxemia. Crit Rev Biomed Eng. 2012;40(4):313-22. 12 pages.

Scheff et al., Translational applications of evaluating physiologic variability in human endotoxemia. J Clin Monit Comput. Aug. 2013;27(4):405-15.

Scheff et al., Predicting critical transitions in a model of systemic inflammation. J Theor Biol. Dec. 7, 2013;338:9-15. doi: 10.1016/j.jtbi.2013.08.011. Epub Aug. 21, 2013.

Seely et al., Complex systems and the technology of variability analysis. Crit Care. Dec. 2004;8(6):R367-84. Epub Sep. 22, 2004.

Shnidman, Binary integration for Swerling target fluctuations. IEEE Trans of Aerospace and Electronic Systems. Jul. 1998;34(3):1043-53.

Sugimoto et al., Distribution and function of prostanoid receptors: studies from knockout mice. Prog Lipid Res. Jul. 2000;39(4):289-314.

Sun et al., Development of an infection screening system for entry inspection at airport quarantine stations using ear temperature, heart and respiration rates. Conf Proc IEEE Eng Med Biol Soc. Jul. 2013;2013:6716-19.

Tracey, The inflammatory reflex. Nature. Dec. 19-26, 2002;420(6917):853-9.

Wahl-Jensen et al., Ebola virion attachment and entry into human macrophages profoundly effects early cellular gene expression. PLoS Negl Trop Dis. Oct. 2011;5(10):e1359(1-16). doi: 10.1371/journal.pntd.0001359. Epub Oct. 18, 2011.

Wilkens et al., Cardiac and microcirculatory effects of different doses of prostaglandin E1 in man. Eur J Clin Pharmacol. 1987;33(2):133-7.

Williamson et al., Vocal biomarkers of depression based on motor incoordination. Proc of the 3rd ACM Intl Workshop on 7udio/visual emotion challenge (AVEC'13). Oct. 21, 2013. Barcelona, Spain. pp. 41-48.

Williamson et al., A biocompatible microdevice for core body temperature monitoring in the early diagnosis of infectious disease. Biomed Microdevices. Mar. 2007;9(1):51-60.

Williamson et al., Seizure prediction using EEG spatiotemporal correlation structure. Epilepsy & Behavior. Oct. 2012;25(2):230-8.

Williamson et al., Detecting and tracking gait asymmetries with wearable accelerometers. IEEE Conf Paper. IEEE Intl Conf on Body Sensor Networks. Jun. 2015; 6 pages.

Williamson et al., Individualized detection of ambulatory distress in the field using wearable sensors. IEEE Conf Paper. IEEE Intl Conf on Body Sensor Networks. May 2013; 6 pages.

Williamson et al., Forecasting respiratory collapse: Theory and practice for averting life-threatening infant apneas. Resp Physiol & Neurobiol. Nov. 1, 2013;189(2):223-31.

Zou et al., Receiver-operating characteristic analysis for evaluating diagnostic tests and predictive models. Circulation. Feb. 6, 2007;115(5):654-7.

\* cited by examiner

| Feature | Day 2 | Day 3 | Day 4 | Day 5 | Day 6 | Day 7 |
|---|---|---|---|---|---|---|
| | Pulmonary | ECG | ECG | Temp | Temp | Temp |
| | BP | Pulmonary | BP | ECG | ECG | BP |
| | ECG | | Temp | BP | Pulmonary | ECG |

FIG. 9

METHODS AND SYSTEMS FOR PRE-SYMPTOMATIC DETECTION OF EXPOSURE TO AN AGENT

CROSS REFERENCE TO RELATED APPLICATION

This application claims the benefit under 35 U.S.C. § 119(e) of U.S. Provisional Application No. 62/193,961, filed on Jul. 17, 2015, entitled "METHODS AND SYSTEMS FOR PRE-FEVER INFECTION DETECTION," which is incorporated herein by reference in its entirety.

STATEMENT REGARDING FEDERALLY SPONSORED RESEARCH

This invention was made with Government support under Contract No. FA8721-05-C-0002 awarded by the U.S. Air Force. The Government has certain rights in the invention.

TECHNICAL FIELD

In general, this disclosure relates to pre-symptomatic detection of exposure to a chemical or biological agent, and in particular, to systems and methods for pre-symptomatic detection of infection or intoxication using physiological data.

BACKGROUND

Traditional biological infection or chemical intoxication detection occurs after agent exposure results in overt symptoms, and relies on specialized technology not appropriate for field use. New approaches allowed by high-throughput sequencing have shown the promise of pre-symptomatic detection using genomic or transcriptional expression profiles in the host. However, these approaches suffer from often prohibitively steep logistic burdens and associated costs (cold chain storage, equipment requirements, extremely qualified operators, serial sampling). Indeed, most infections presented clinically are never definitively determined etiologically, much less serially sampled. Furthermore, molecular diagnostics are rarely used until patient self-reporting and presentation of overt clinical symptoms, such as fever. Past physiological signal based early infection detection work has been almost exclusively focused on bacterial infection and largely centered upon higher time resolution analysis of body core temperature, advanced analyses of strongly-confounded signals such as heart rate variability, or social dynamics, or sensor data fusion from already symptomatic (febrile) viral-infected individuals. While progress has been made in developing techniques for signal-based early warning of bacterial infections, there appear to be no efforts in extending these techniques to possibly life-threatening viral infections or toxic chemical exposure/intoxication.

SUMMARY

Systems and methods are disclosed herein for detection of exposure to an agent. Physiological data regarding a patient that was recorded during a first time interval is received by at least one processor. One or more features are extracted from the physiological data, wherein each feature is representative of the physiological data during the first time interval. A plurality of classifiers is identified, wherein each classifier is trained using training data for a respective specific post-exposure time interval. For each classifier and based on a respective subset of the one or more features, a patient state classification that indicates an initial prediction of whether the patient has been exposed to the agent is determined. An indication is provided of a prediction that the patient has been exposed to the agent when a number of patient state classifications indicating a positive initial prediction that the patient has been exposed to the agent exceeds a first threshold.

In one embodiment, the above-recited steps are repeated for one or more additional first time intervals, and an indication that the patient has been exposed to the agent is provided when a number of indications that the patient has been exposed to the agent exceeds a second threshold.

In one embodiment, each classifier in the plurality of classifiers is a respective random forest classifier, and determining the patient state classification includes determining whether a third threshold number of trees in the respective random forest classifier indicates exposure to the agent.

In one embodiment, the respective specific post-exposure time interval corresponds to a 24 hour time period after exposure to the agent, and each classifier in the plurality of classifiers corresponds to a different 24 hour time period after exposure.

In one embodiment, a first respective specific post-exposure time interval corresponds to a post-exposure and pre-symptomatic time interval and a second respective specific post-exposure time interval corresponds to a post-exposure and post-symptomatic time interval.

In one embodiment, an additional classifier is used that is trained on training data for a pre-exposure time interval. The training data for the pre-exposure time interval may be taken from the patient, or from a population of patients not including the patient.

In one embodiment, the agent is selected from the group consisting of a chemical agent, a biological agent, a viral pathogen, and a bacterial pathogen.

In one embodiment, the one or more features are derived from pulmonary data, blood pressure data, electrocardiography data, and temperature data.

In one embodiment, the respective specific post-exposure time interval for a first classifier in the plurality of classifiers is approximately two days after exposure, and the first classifier uses pulmonary data, blood pressure data, and electrocardiography data.

In one embodiment, the respective specific post-exposure time interval for a second classifier in the plurality of classifiers is approximately three days after exposure, and the second classifier uses electrocardiography data and pulmonary data.

In one embodiment, the respective specific post-exposure time interval for a third classifier in the plurality of classifiers is approximately four days after exposure, and the first classifier uses electrocardiography data, blood pressure data, and temperature data.

In one embodiment, the respective specific post-exposure time interval for a fourth classifier in the plurality of classifiers is approximately five days after exposure, and the fourth classifier uses temperature data, electrocardiography data, and blood pressure data.

In one embodiment, the respective specific post-exposure time interval for a fifth classifier in the plurality of classifiers is approximately six days after exposure, and the fifth classifier uses temperature data, electrocardiography data, and pulmonary data.

According to another aspect, the disclosure relates to a system to carry out the method described above. In particular, a system for predicting whether a patient has been exposed to an agent is described. The system comprises at least one processor configured to receive physiological data regarding the patient that was recorded during a first time interval, extract one or more features from the physiological data, wherein each feature is representative of the physiological data during the first time interval. The at least one processor is further configured to identify a plurality of classifiers, wherein each classifier is trained using training data for a respective specific post-exposure time interval. For each classifier and based on a respective subset of the one or more features, a patient state classification that indicates an initial prediction of whether the patient has been exposed to the agent is determined. An indication of a prediction that the patient has been exposed to the agent is provided when a number of patient state classifications indicating a positive initial prediction that the patient has been exposed to the agent exceeds a first threshold.

In one embodiment, the above-recited steps are repeated for one or more additional first time intervals, and an indication that the patient has been exposed is provided when a number of indications that the patient has been exposed to the agent exceeds a second threshold.

In one embodiment, each classifier in the plurality of classifiers is a respective random forest classifier, and determining the patient state classification includes determining whether a third threshold number of trees in the respective random forest classifier indicates exposure to the agent.

In one embodiment, the respective specific post-exposure time interval corresponds to a 24 hour time period after exposure to the agent, and each classifier in the plurality of classifiers corresponds to a different 24 hour time period after exposure.

In one embodiment, a first respective specific post-exposure time interval corresponds to a post-exposure and pre-symptomatic time interval and a second respective specific post-exposure time interval corresponds to a post-exposure and post-symptomatic time interval.

In one embodiment, an additional classifier is used that is trained on training data for a pre-exposure time interval. The training data for the pre-exposure time interval may be taken from the patient, or from a population of patients not including the patient.

In one embodiment, the agent is selected from the group consisting of a chemical agent, a biological agent, a viral pathogen, and a bacterial pathogen.

In one embodiment, the one or more features are derived from pulmonary data, blood pressure data, electrocardiography data, and temperature data.

In one embodiment, the respective specific post-exposure time interval for a first classifier in the plurality of classifiers is approximately two days after exposure, and the first classifier uses pulmonary data, blood pressure data, and electrocardiography data.

In one embodiment, the respective specific post-exposure time interval for a second classifier in the plurality of classifiers is approximately three days after exposure, and the second classifier uses electrocardiography data and pulmonary data.

In one embodiment, the respective specific post-exposure time interval for a third classifier in the plurality of classifiers is approximately four days after exposure, and the first classifier uses electrocardiography data, blood pressure data, and temperature data.

In one embodiment, the respective specific post-exposure time interval for a fourth classifier in the plurality of classifiers is approximately five days after exposure, and the fourth classifier uses temperature data, electrocardiography data, and blood pressure data.

In one embodiment, the respective specific post-exposure time interval for a fifth classifier in the plurality of classifiers is approximately six days after exposure, and the fifth classifier uses temperature data, electrocardiography data, and pulmonary data.

According to another aspect, the disclosure relates to methods and a system for providing infection detection classifiers, the system comprising a receiver configured to receive a plurality of data sets, wherein each data set includes physiological data related to a patient, and a processor configured to separate the plurality of data sets into a training set and a testing set, wherein each data set in the training set is associated with a time of infection, generate a plurality of classifiers, wherein each classifier is based on a time period since the time of infection, identify, with each classifier, a score that indicates a likelihood of an infection state classification, and configure each classifier to output the infection state classification when the score exceeds a threshold.

BRIEF DESCRIPTION OF THE DRAWINGS

The above and other features of the present disclosure, including its nature and its various advantages, will be more apparent upon consideration of the following detailed description, taken in conjunction with the accompanying drawings in which:

FIG. 9 is a table indicating the physiological data that are important to patient state classification for the days after pathogen exposure;

DETAILED DESCRIPTION

Figure 1:
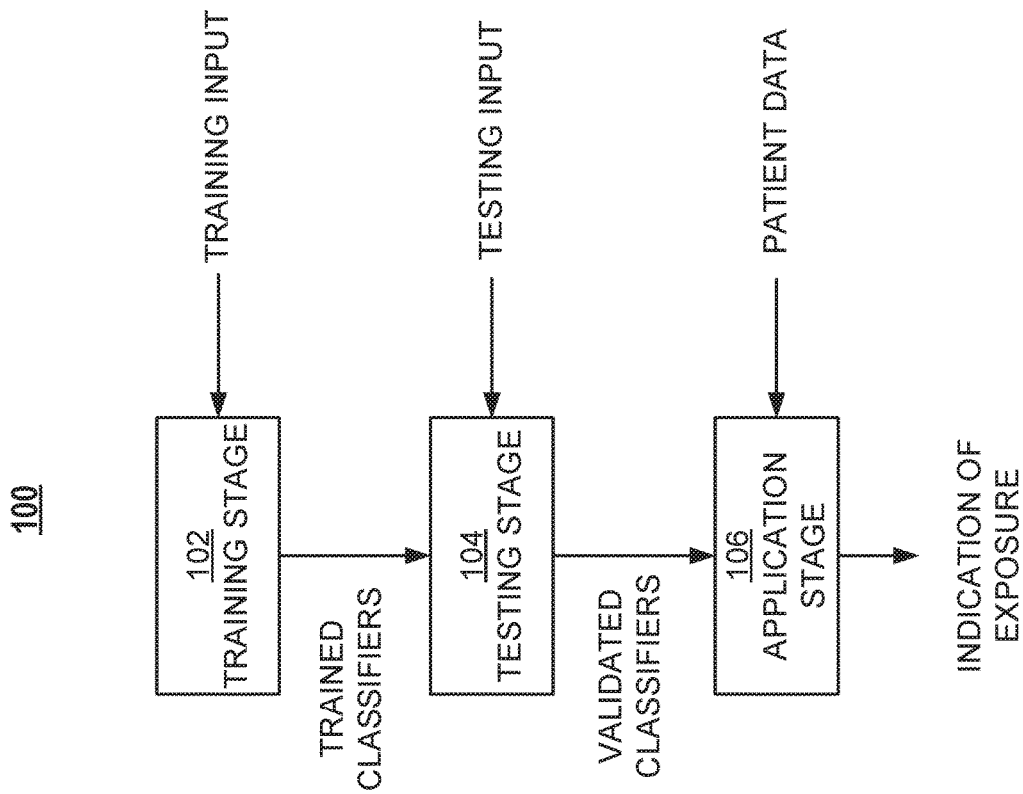
FIG. 1 is a block diagram of a classification system for determining a physiological state classification associated with physiological data, according to an illustrative implementation of the disclosure.

To provide an overall understanding of the systems and methods described herein, certain illustrative embodiments will now be described, including a system for pre-symptomatic detection of exposure to an agent using physiological data classifiers. However, it will be understood by one of ordinary skill in the art that the systems and methods described herein may be adapted and modified as is appropriate for the application being addressed and that the systems and methods described herein may be employed in other suitable applications, and that such other additions and modifications will not depart from the scope thereof. Generally, the computerized systems described herein may comprise one or more local or distributed engines, which include a processing device or devices, such as a computer, microprocessor, logic device or other device or processor that is configured with hardware, firmware, and software to carry out one or more of the computerized methods described herein.

The disclosure describes, among other things, technical details of methods and systems for providing early warning of viral infections by using physiological monitoring before symptoms become apparent. As used herein, the term "agent" includes a chemical substance, a biological substance, a viral pathogen, a bacterial pathogen, or any suitable combination thereof. The systems and methods of the present disclosure involve a high sensitivity and low specificity (that is, not informative of particular pathogens) processing and detection technique. The data is analyzed and anomalies are detected. The anomalies may indicate a pre-symptomatic infection, and may provide early warning about an infection well before an onset of fever. Quantitative analyses of the physiological data are conducted by extracting several features, including summary statistics, and performing classification, which may be done by random forest classifiers trained on respective post agent exposure time intervals, in an illustrative embodiment. Random forest classifiers are described herein by way of example only, and one of ordinary skill in the art will understand that other types of classifiers may be used without departing from the scope of the present disclosure, such as k-nearest neighbors classifiers and naive Bayes classifiers. In a first step, classifiers are trained on a set of physiological training data for which the patients' physiological states are known. A physiological state may correspond to the progression of an infection within a patient, the determination whether a patient was ever likely exposed to a agent, or any suitable classification based on physiological data and related to infection detection. In a second step, the classifiers are tested on a set of physiological testing data for their ability to detect infection in patients whose agent exposure time is known. In a third step, the classifiers are applied to a patient for which the physiological state is unknown. The classifiers will provide a detection indication when the number of classifiers predicting an infection in a given time interval exceeds a threshold, which is referred to as a detection. The classifiers will provide a declaration indication when the number of detection indications exceeds a threshold condition, which is referred to as a declaration. Detection and declaration indications may take any suitable format to indicate to users or elements of the present disclosure that the conditions for detection and declaration have been met. The systems and methods described herein demonstrate pre-symptomatic diagnostic potential, and may provide early warning about an infection well before an onset of fever. The time between the final declaration and the onset of fever is referred to herein as the "early warning time."

The systems and methods of the present disclosure may be described in more detail with reference to FIGS. 1-12. More particularly, an exemplary system for providing disease classification and its components are described with reference to FIGS. 1-5. The system may provide disease classification as described with reference to flow charts in FIGS. 6-8. In addition, exemplary classifier outputs are described with reference to FIGS. 9-12.

FIG. 1 is an illustrative block diagram of a classification system 100 for determining a physiological state classification associated with physiological data. The system 100 includes a training stage 102, a testing stage 104, and an application stage 106. Inputs to the system 100 include training input data to train a set of classifiers, testing input data to test the set of trained classifiers, and data recorded from a patient. The system 100 uses the trained and tested classifiers and the patient data to provide a predicted physiological state classification for the patient.

The training stage 102 receives a set of training input data and provides a set of trained classifiers to the testing stage 104. The set of training input data includes a set of training physiological data recorded from a first group of patients and a set of the times the patients were exposed to one or more agents. The components of the training stage 102 are described in detail in relation to FIG. 2, and the training stage 102 may operate on the training input data according to the method as described in relation to FIG. 6. In particular, the training stage 102 may select subsets of the training input data and train a classifier on each selected subset, for example by training each classifier on data from a respective time period, e.g. 24 hours, after agent exposure.

The testing stage 104 receives the set of trained classifiers from the training stage 102 and a set of testing input data. The set of testing input data includes a set of testing physiological data recorded from a second group of patients and a set of the times the patients were exposed to agents. The components of the testing stage 104 are described in detail in relation to FIG. 3, and the testing stage 104 may operate on the testing input data and the trained classifiers according to the method as described in relation to FIG. 7. In particular, the testing stage 104 may compare detection indications from the trained classifiers operating on the testing input data and compare the infection state classifications predicted by the detection indications to the corresponding set of actual physiological states from the second group of patients. If there is a sufficient match between the predicted and actual physiological states, the testing stage 104 validates the classifiers and provides the validated classifiers to the application stage 106.

The application stage 106 receives the set of validated classifiers from the testing stage 104 and physiological data recorded from a patient, and the agent exposure of the patient may be unknown. The components of the application stage 106 are described in detail in relation to FIG. 4, and the application stage 106 may operate on the patient data and the validated classifiers according to the method as described in relation to FIG. 7. In particular, the application stage 106 may aggregate patient state classifications from the validated classifiers operating on the patient data to determine infection detection indications and declaration indications, which are defined in relation to FIG. 7. The indications of infection may be provided by the system 100 to a user such as a medical professional.

Figure 2:
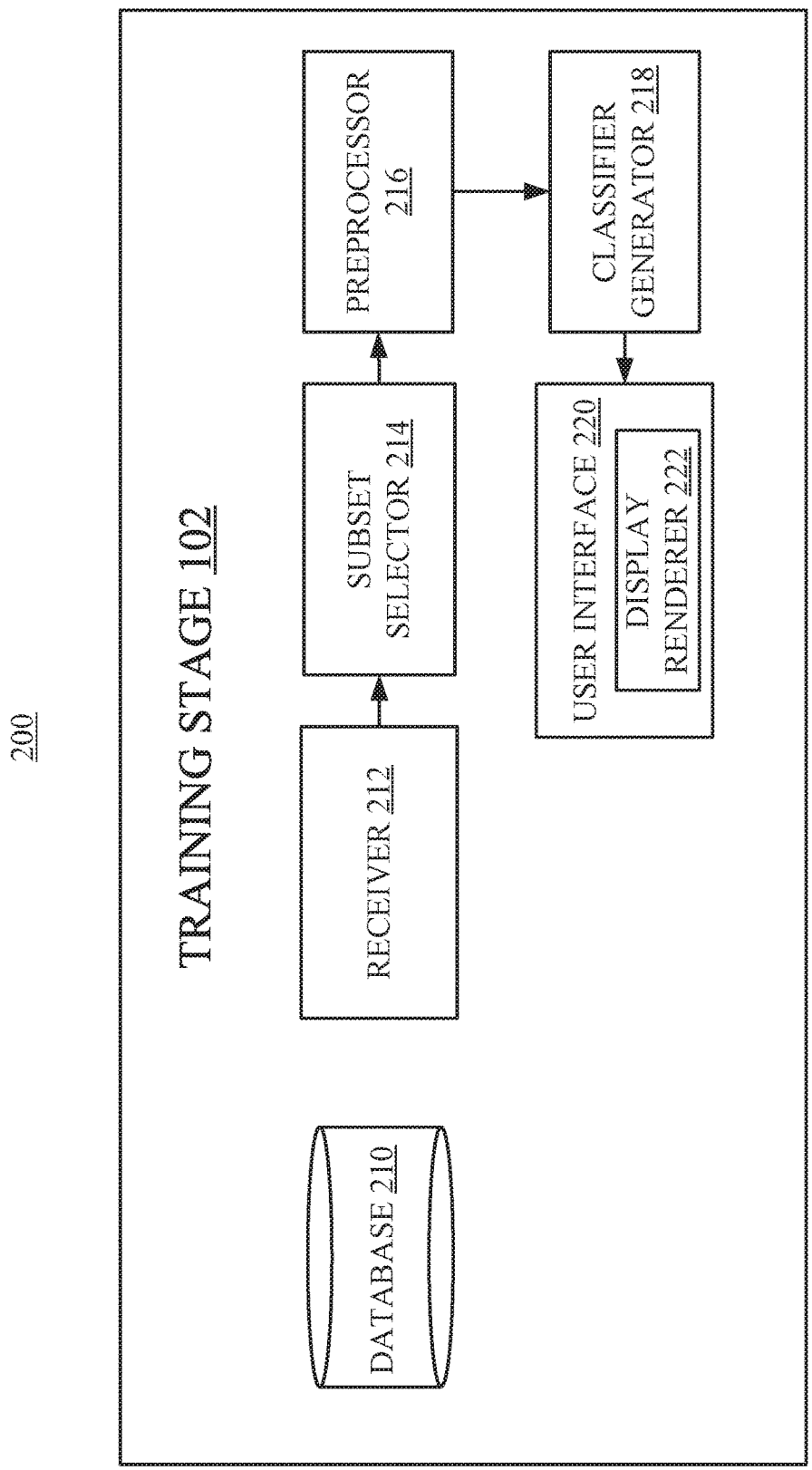
FIG. 2 is a block diagram of a training system for training a set of classifiers on physiological data, according to an illustrative implementation of the disclosure.

FIG. 2 is an illustrative block diagram of a training system 200 for training a set of classifiers on physiological data. The training stage 102 includes several components for executing the processes described herein. In particular, the training stage 102 includes a database 210, a receiver 212, a subset selector 214, a preprocessor 216, a classifier generator 218, and a user interface 220 that includes a display renderer 222. The training stage 102 may operate on training input data according to the method as described in relation to FIG. 6. The database 210 may be used to store any data related to training a set of classifiers as described herein.

The training stage 102 receives training input data over the receiver 212. The receiver 212 may provide an interface with a data source, which may transmit physiological training data and agent exposure data to the training stage 102. The physiological training data may be recorded from a first group of patients with respect to known agent exposure timing for the first group of patients and transmitted to the receiver 212. The physiological data may be recorded by any suitable means including implanted and wearable sensors. In particular, the training physiological data may include a number of physiological measurements, such as electrocardiogram data, pulmonary data, blood pressure data, temperature data, neurocognitive data (EEG), gait and ambulation measurements (actigraphy), speech data, muscle electrophysiology (EMG) data, pupil diameter measurements, sweat rate and salinity measurements, breath exhalate chemical analysis, and any other suitable physiological measurement.

After the training data are received, the subset selector 214 divides the training data into temporal subsets that include data recorded during specific time intervals, e.g. one time interval for each 12 hour period, 24 hour period, 36 hour period, or any other suitable time interval after agent exposure. In some implementations, the subset selector 214 selects only a portion, e.g. two thirds, one half, or any suitable portion, of the training data to be used in the training stage. The remaining training data may be reserved for use in the testing stage to cross validate the classifiers generated by the training stage.

The training data selected by the subset selector 214 is communicated to the preprocessor 216, which processes the training data to convert the data into a suitable form for performing classification. The preprocessor 216 may be used to eliminate short term fluctuations, eliminate diurnal rhythms, divide the data into time intervals, generate suitable summary statistics for each type of physiological data to be used as features for classification for each time interval, or any suitable combination thereof. In an exemplary implementation, the preprocessor 216 divides the training data into time intervals of a suitable length, e.g. 5, 10, 15, 30, 45, or 60 minutes, and calculates a mean value for each interval in order to eliminate short term fluctuations. To eliminate diurnal rhythms, each data point may be represented as a percent difference from the original point value and the mean value calculated for the respective time interval. The preprocessor 216 may then divide the training data into time intervals of the same or a different length, e.g. 15 minutes, 30 minutes, 60 minutes, or any suitable length of time, and extract suitable features for each interval. For example, the preprocessor may calculate, for each time interval, a mean value, a standard deviation, and quartiles of the data values, which may be percent differences. These statistics may be used as the features that characterize the physiological data and may be calculated for any suitable physiological data, such as pulse data, ECG data, pulmonary data, blood pressure data, and temperature data, and input to the patient state classifiers. These examples of physiological data are described by way of example only, and one of ordinary skill in the art will understand that other features of physiological data may be extracted without departing from the scope of the present disclosure. The preprocessor 216 may also be configured to identify and remove outliers from the physiological data. The determination that a data point is an outlier, e.g. representative of a transient physiological anomaly, representative of a measurement error, or that is generally unsuitable for inclusion in the classification, may be made by the preprocessor 216.

The classifier generator 218 uses the features extracted by the preprocessor 216 to generate a patient state classifier for each time interval chosen by the subset selector 214. In some implementations, there is one classifier trained for each day, 12 hour interval, 36 hour interval, 48 hour interval, or any other suitable interval of data recorded after the patient was exposed to a agent as well as a baseline classifier that characterizes pre-exposure somatic function. In some implementations, the classifiers are random forest classifiers, each of which uses a set of decision trees to generate a final classification decision. In some implementations the random forests output a classification decision as well as a score indicating the proportion of trees in the forest whose individual output matched the forest classification or the proportion of trees whose classification indicates the presence of an infection. The random forest classifiers may be calibrated to output a patient state classification that indicates a prediction of the patient having been exposed to a agent only when the score exceeds a threshold, which may be determined by a target false prediction rate, sensitivity, specificity, or any suitable means. Additionally, the random forest classifiers may be used to determine the feature importance metrics of the input training features. The feature importance metric of a feature indicates how important a feature is to determining the final classification. The random forest classifiers may further output a list of the features that indicates the respective importance metric for each feature. The lists of predictively important features and any other suitable model output, including classifications and scores, can be output to a user via display renderer 222 or any suitable means.

In some implementations, the classifier generator 218 will train an intermediate classifier to identify the most predictive features, based on their feature importance metrics, e.g. those metrics that exceeds a threshold or the most predictive proportion of the features. A final classifier is then trained using the most predictive features. In some implementations, the user may specify which types of physiological data are used, e.g. classifiers that only use ECG data.

Figure 3:
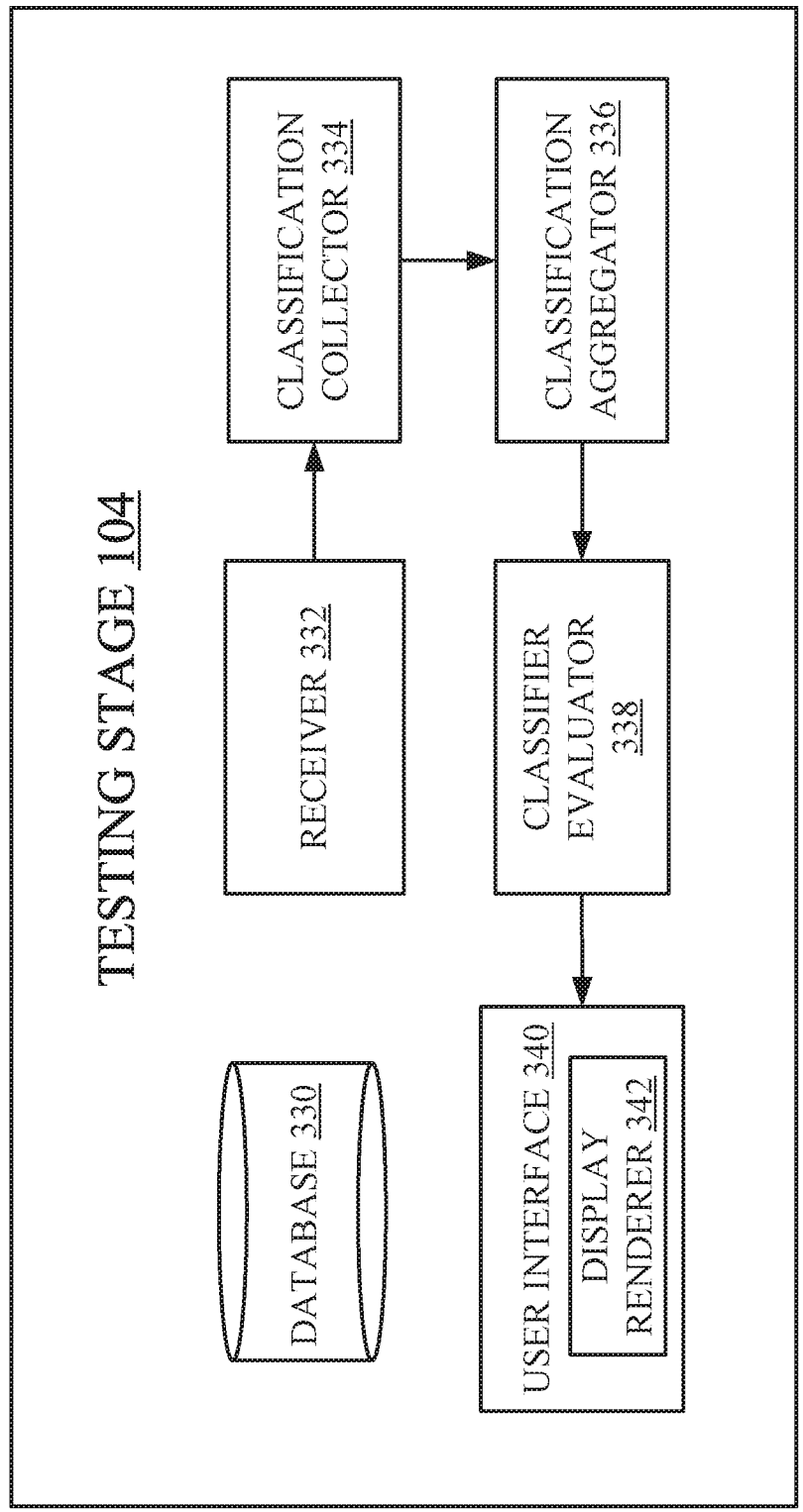
FIG. 3 is a block diagram of a testing system for testing a set of trained classifiers on physiological data, according to an illustrative implementation of the disclosure.

FIG. 3 is a block diagram of a testing system 300 for testing a set of trained classifiers on physiological data, according to an illustrative implementation of the disclosure. The testing stage 104 includes several components for executing the processes described herein. In particular, the testing stage 104 includes a database 330, a receiver 332, a classification collector 334, a classification aggregator 336, a classifier evaluator 338, and a user interface 340 including a display renderer 342. The testing stage 104 may operate on testing input data and a set of trained classifiers according to the method described in relation to FIG. 7. The database 330 may be used to store any data related to testing a set of classifiers as described herein.

The testing stage 104 receives testing input data and a set of trained classifiers over the receiver 332. The receiver 332 may provide an interface with a data source, which may transmit testing physiological data and corresponding agent exposure data to the testing stage 204. The testing physiological data may be recorded from a second group of patients (i.e., which may be different from the first group of patients making up the set of testing physiological data), and the agent exposure of the second group of patients may be known and transmitted to the receiver 332. In some implementations, the second group of patients is a portion of the testing data that was set aside during the training stage 102. Patient data set aside during the training stage 102 is not used to train the classifiers and can, therefore, be used to cross validate the classifiers. The patients within and across the first and second groups may not be infected with the same disease. Patients used for cross validation may not be infected with any disease. The receiver 332 may also form an interface with the training stage 102 to receive a set of trained classifiers from the training stage 102. In particular, each trained classifier in the set of trained classifiers may be trained on physiological data from a specific post agent exposure time interval.

After the testing data and the set of classifiers are received, the classification collector 334 collects classifications from the trained classifiers based on the physiological record from each patient in the second group of patients. The classifications correspond to candidate physiological state classifications that are output for a given time interval, e.g. 15 minutes, 30 minutes, or 1 hour, based on the likelihood of infection determined by each trained classifier. In some implementations, for each patient record in the set of testing physiological data and each time interval, the classification collector 334 determines whether the number of patient state classifications indicating infection meets or exceeds a threshold (e.g. a threshold level of 1 out of 6 classifiers or 2 out of 7 classifiers) and outputs an infection detection indication.

After the classifications for a time interval have been collected, the classification aggregator 336 aggregates the classifications. The classification aggregator 336 combines the classifications and detection indications from each time interval for a patient. When the number of infection detection indications in a certain number of recent time intervals exceeds a threshold, the classification aggregator 336 outputs an indication that the patient is ill, a declaration indication.

After the classifications are aggregated, the classifier evaluator 338 performs a validation of the classifiers. In particular, the classifier evaluator 338 compares the infection detections and declarations to the known physiological states of the second group of patients to determine a level of accuracy of the classifiers and to compare the declaration of illness to the onset of febrile symptoms. For example, the classifier evaluator 338 may determine that the classifiers are validated if the number of correctly declared illnesses exceeds a threshold or if the diagnoses are being made sufficiently close to agent exposure. The threshold may be a fixed number or a percentage and may be provided by a user over the user interface 340. If the classifier evaluator 338 determines that the trained classifiers are invalid, the testing stage 104 may provide an instruction to the training stage 102 to repeat the training process (e.g. trying a different set of features, a different number of classifiers, or a change in any other suitable parameter in the training process). For example, the testing stage 104 may return the rejected classifiers to the training stage 202. The rejected classifiers may be retrained using the most predictive features identified in the rejected classifier, based on their feature importance metrics, e.g. those metrics that exceeds a threshold or the most predictive proportion of the features. A new classifier is then trained using the most predictive features. These steps may be repeated until a set of classifiers is identified that satisfies the criterion required by the classifier evaluator 338. The testing stage 104 then provides the validated set of classifiers to the application stage 206.

Figure 4:
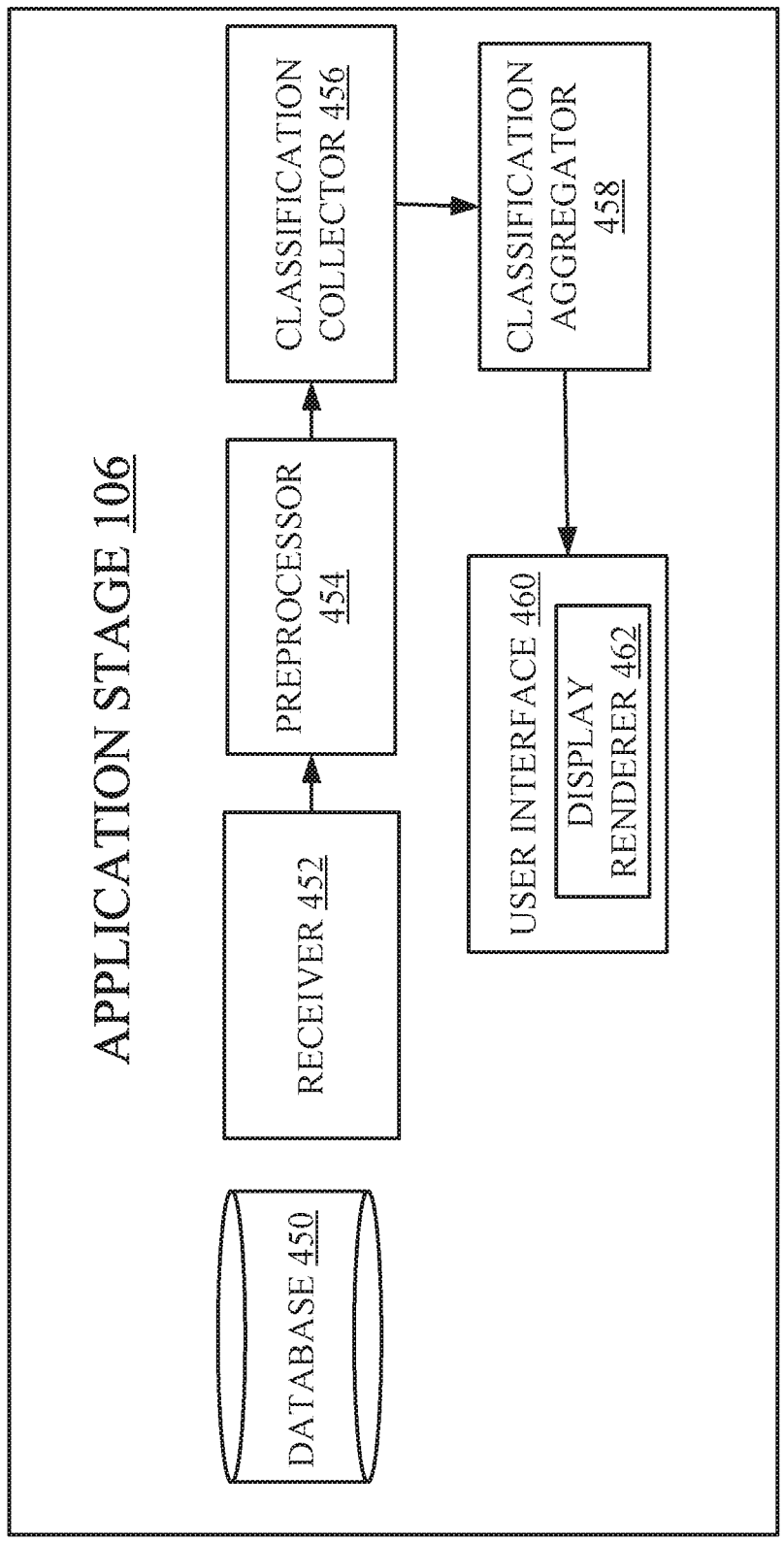
FIG. 4 is a block diagram of an application system for using trained and tested classifiers to determine a physiological state classification associated with physiological data, according to an illustrative implementation of the disclosure.

FIG. 4 is a block diagram of an application system 400 for using trained and tested classifiers to determine a physiological state classification associated with physiological data, according to an illustrative implementation of the disclosure. The application stage 106 includes several components for executing the processes described herein. In particular, the application stage 106 includes a database 450, a receiver 452, a preprocessor 454, a classification collector 456, a classification aggregator 458, and a user interface 460 including a display renderer 462. The testing stage 104 may operate on testing input data and a set of trained classifiers according to the method described in relation to FIG. 7. The database 450 may be used to store any data related to testing a set of classifiers as described herein.

The application stage 106 receives a set of trained classifiers over the receiver 452. The receiver 452 may provide an interface with a data source, which transmits physiological data related to a patient to the application stage 106. The physiological data may be recorded from a patient that was not included in the training or testing groups of patients, and the agent exposure of the patient may be unknown. The recording may be done using high resolution monitors, surgically implanted monitors, wearable monitors, or any suitable physiological monitor. The receiver 452 may also form an interface with the training stage 102 to receive a set of trained classifiers from the training stage 102. In particular, each trained classifier in the set of trained classifiers may be trained on physiological data from a specific post agent exposure time interval.

Patient physiological data communicated to the receiver 452 is communicated to preprocessor 454, which processes the training data to convert the data into a suitable form for performing classification. The preprocessor 454 may be used to eliminate short term fluctuations, eliminate diurnal rhythms, divide the data into time intervals, generate suitable summary statistics for each type of physiological data to be used as features for classification for each time interval, or any suitable combination thereof. In an exemplary implementation, the preprocessor 454 divides the training data into time intervals of a suitable length, e.g. 5, 10, 15, 30, 45, or 60 minutes, and calculates a mean value for each interval in order to eliminate short term fluctuations. To eliminate diurnal rhythms, each data point may be represented as a percent difference from the original point value and the mean value calculated for the respective time interval. The preprocessor 454 may then divide the training data into time intervals of the same or a different length, e.g. 15 minutes, 30 minutes, 60 minutes, or any suitable length of time, and extract suitable features for each interval. For example, the preprocessor may calculate, for each time interval, a mean value, a standard deviation, and quartiles of the data values, which may be percent differences. These statistics may be used as the features that characterize the physiological data and may be calculated for any suitable physiological data, such as pulse data, ECG data, pulmonary data, blood pressure data, and temperature data, and input to the patient state classifiers. These examples of physiological data are described by way of example only, and one of ordinary skill in the art will understand that other features of physiological data may be extracted without departing from the scope of the present disclosure. The preprocessor 454 may also be configured to identify and remove outliers from the physiological data. The determination that a data point is an outlier, e.g. representative of a transient physiological anomaly, representative of a measurement error, or that is generally unsuitable for inclusion in the classification, may be made by the preprocessor 454.

After the set of classifiers are received and as the physiological data is received and preprocessed, the classification collector 456 collects classifications from the set of trained classifiers based on the physiological data from the patient. The classifications correspond to candidate physiological state classifications that are output for a given time interval, e.g. 2 minutes, 5 minutes, 15 minutes, 30 minutes, or 1 hour, based on the likelihood of infection determined by each trained classifier. This time interval may be based on an expected speed of infection or intoxication. For example, when analyzing a likelihood of a chemical exposure, a time interval of 2 minutes may be used. In some implementations, the patient's physiological data is streamed to the receiver 452 in real time. In some implementations, the patient's physiological data is downloaded from a storage medium to the receiver 452 or database 450. In some implementations, for each time interval, the classification collector 456 determines whether the number of patient state classifications indicating infection meets or exceeds a threshold (e.g. a threshold level of 1 out of 6 classifiers or 2 out of 7 classifiers) and outputs an infection detection indication. In some implementations, the classification collector 456 applies each classifier in the set of classifiers to the same time interval. In some implementations, the classification applies each classifier to respective time intervals that are spaced apart by an amount equal to the length of the time period on which each classifier was trained. For example, if the classifiers were trained on 24 hour periods of post exposure data, then the classification collector 456 applies the classifiers to time intervals that are 24 hours apart, and the classification collector 456 applies this process once for each classifier in order to position each classifier as the most recent, since the time of agent exposure is unknown. This process can allow for early detection of infection as well as an estimated time of exposure.

After the classifications for a time interval have been collected, the classification aggregator 458 aggregates the classifications. The classification aggregator 458 combines the classifications and detection indications from each time interval for a patient. When the number of infection detection indications in a certain number of recent time intervals exceeds a threshold, the classification aggregator 458 outputs an indication that the patient is ill. This may be referred to herein as a declaration indication, which may be displayed to a clinician via user interface 460, display renderer 462, or any suitable means.

Figure 5:
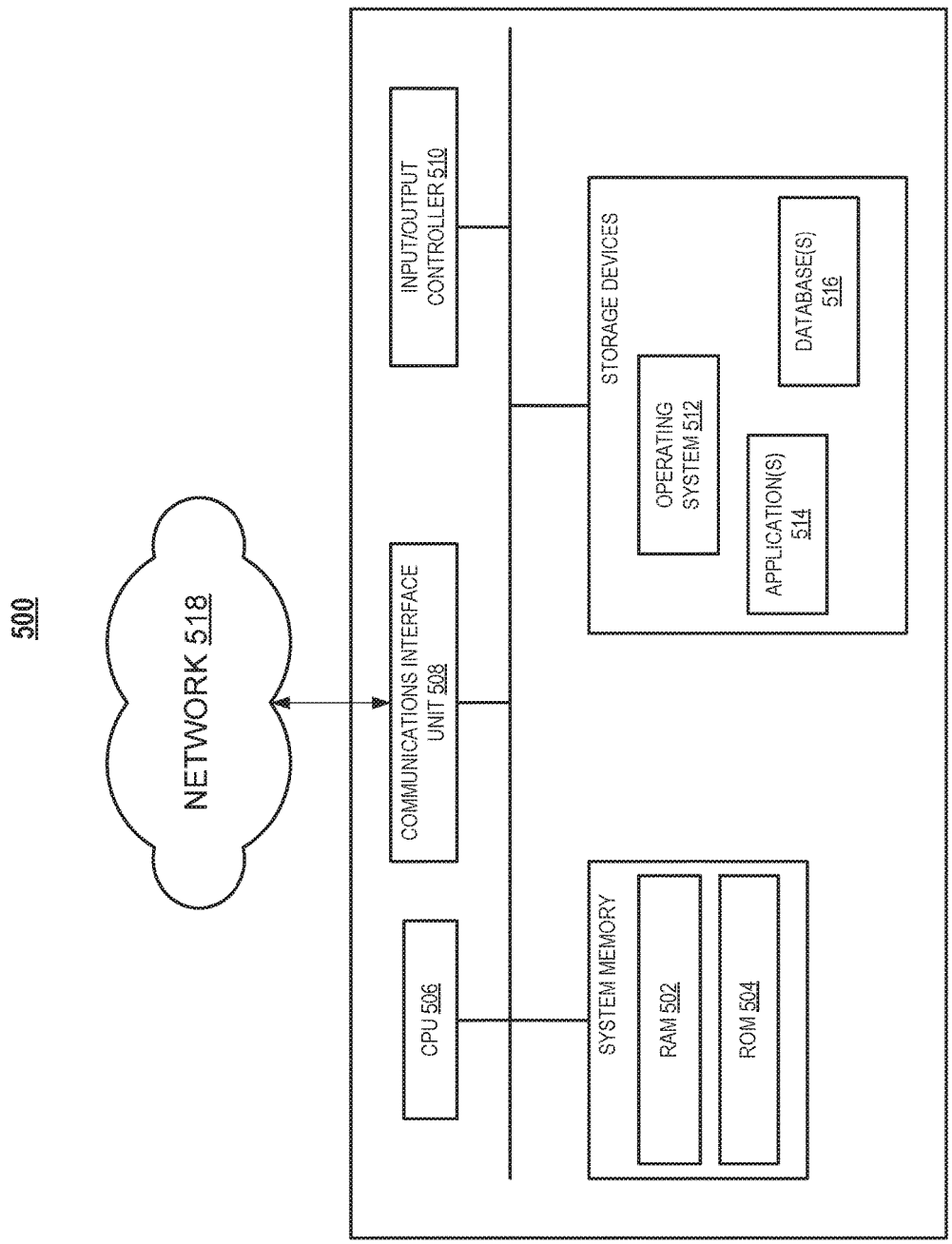
FIG. 5 is a block diagram of a computing device for performing any of the processes described herein, according to an illustrative implementation of the disclosure.

FIG. 5 is a block diagram of a computing device for performing any of the processes described herein, according to an illustrative embodiment. Each of the components of these systems may be implemented on one or more computing devices 500. In certain aspects, a plurality of the components of these systems may be included within one computing device 500. In certain implementations, a component and a storage device may be implemented across several computing devices 500.

The computing device 500 comprises at least one communications interface unit, an input/output controller 510, system memory, and one or more data storage devices. The system memory includes at least one random access memory (RAM 502) and at least one read-only memory (ROM 504). All of these elements are in communication with a central processing unit (CPU 506) to facilitate the operation of the computing device 500. The computing device 500 may be configured in many different ways. For example, the computing device 500 may be a conventional standalone computer or, alternatively, the functions of computing device 500 may be distributed across multiple computer systems and architectures. In FIG. 5, the computing device 500 is linked, via network or local network, to other servers or systems.

The computing device 500 may be configured in a distributed architecture, wherein databases and processors are housed in separate units or locations. Some units perform primary processing functions and contain at a minimum a general controller or a processor and a system memory. In distributed architecture implementations, each of these units may be attached via the communications interface unit 508 to a communications hub or port (not shown) that serves as a primary communication link with other servers, client or user computers and other related devices. The communications hub or port may have minimal processing capability itself, serving primarily as a communications router. A variety of communications protocols may be part of the system, including, but not limited to: Ethernet, SAP, SAS™, ATP, BLUETOOTH™, GSM and TCP/IP.

The CPU 506 comprises a processor, such as one or more conventional microprocessors and one or more supplementary co-processors such as math co-processors for offloading workload from the CPU 506. The CPU 506 is in communication with the communications interface unit 508 and the input/output controller 510, through which the CPU 506 communicates with other devices such as other servers, user terminals, or devices. The communications interface unit 508 and the input/output controller 510 may include multiple communication channels for simultaneous communication with, for example, other processors, servers or client terminals in the network 518.

The CPU 506 is also in communication with the data storage device. The data storage device may comprise an appropriate combination of magnetic, optical or semiconductor memory, and may include, for example, RAM 502, ROM 504, flash drive, an optical disc such as a compact disc or a hard disk or drive. The CPU 506 and the data storage device each may be, for example, located entirely within a single computer or other computing device; or connected to each other by a communication medium, such as a USB port, serial port cable, a coaxial cable, an Ethernet cable, a telephone line, a radio frequency transceiver or other similar wireless or wired medium or combination of the foregoing. For example, the CPU 506 may be connected to the data storage device via the communications interface unit 508. The CPU 506 may be configured to perform one or more particular processing functions.

The data storage device may store, for example, (i) an operating system 512 for the computing device 500; (ii) one or more applications 514 (e.g., computer program code or a computer program product) adapted to direct the CPU 506 in accordance with the systems and methods described here, and particularly in accordance with the processes described in detail with regard to the CPU 506; or (iii) database(s) 516 adapted to store information that may be utilized to store information required by the program.

The operating system 512 and applications 514 may be stored, for example, in a compressed, an un-compiled and an encrypted format, and may include computer program code. The instructions of the program may be read into a main memory of the processor from a computer-readable medium other than the data storage device, such as from the ROM 504 or from the RAM 502. While execution of sequences of instructions in the program causes the CPU 506 to perform the process steps described herein, hard-wired circuitry may be used in place of, or in combination with, software instructions for implementation of the processes of the present disclosure. Thus, the systems and methods described are not limited to any specific combination of hardware and software.

Suitable computer program code may be provided for performing one or more functions in relation to performing classification of physiological states based on physiological data as described herein. The program also may include program elements such as an operating system 512, a database management system and "device drivers" that allow the processor to interface with computer peripheral devices (e.g., a video display, a keyboard, a computer mouse, etc.) via the input/output controller 510.

The term "computer-readable medium" as used herein refers to any non-transitory medium that provides or participates in providing instructions to the processor of the computing device 500 (or any other processor of a device described herein) for execution. Such a medium may take many forms, including but not limited to, non-volatile media and volatile media. Non-volatile media include, for example, optical, magnetic, or opto-magnetic disks, or integrated circuit memory, such as flash memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM or EEPROM (electronically erasable programmable read-only memory), a FLASH-EEPROM, any other memory chip or cartridge, or any other non-transitory medium from which a computer can read.

Various forms of computer readable media may be involved in carrying one or more sequences of one or more instructions to the CPU 506 (or any other processor of a device described herein) for execution. For example, the instructions may initially be borne on a magnetic disk of a remote computer (not shown). The remote computer can load the instructions into its dynamic memory and send the instructions over an Ethernet connection, cable line, or even telephone line using a modem. A communications device local to a computing device 500 (e.g., a server) can receive the data on the respective communications line and place the data on a system bus for the processor. The system bus carries the data to main memory, from which the processor retrieves and executes the instructions. The instructions received by main memory may optionally be stored in memory either before or after execution by the processor. In addition, instructions may be received via a communication port as electrical, electromagnetic or optical signals, which are exemplary forms of wireless communications or data streams that carry various types of information.

The systems shown in FIGS. 1-5 may pre-fever infection detection as described with reference to flowcharts in FIGS. 6-8. In particular, the training stage 102 may use the method shown in FIG. 6 to train a set of classifiers on a set of physiological training data. After the set of classifiers are trained, the testing stage may use the method shown in FIG. 7 to validate the set of trained classifiers. Finally, the application stage may use the method shown in FIG. 7 to apply the validated classifiers to a patient's physiological data to identify a predicted physiological state of the patient.

Figure 6:
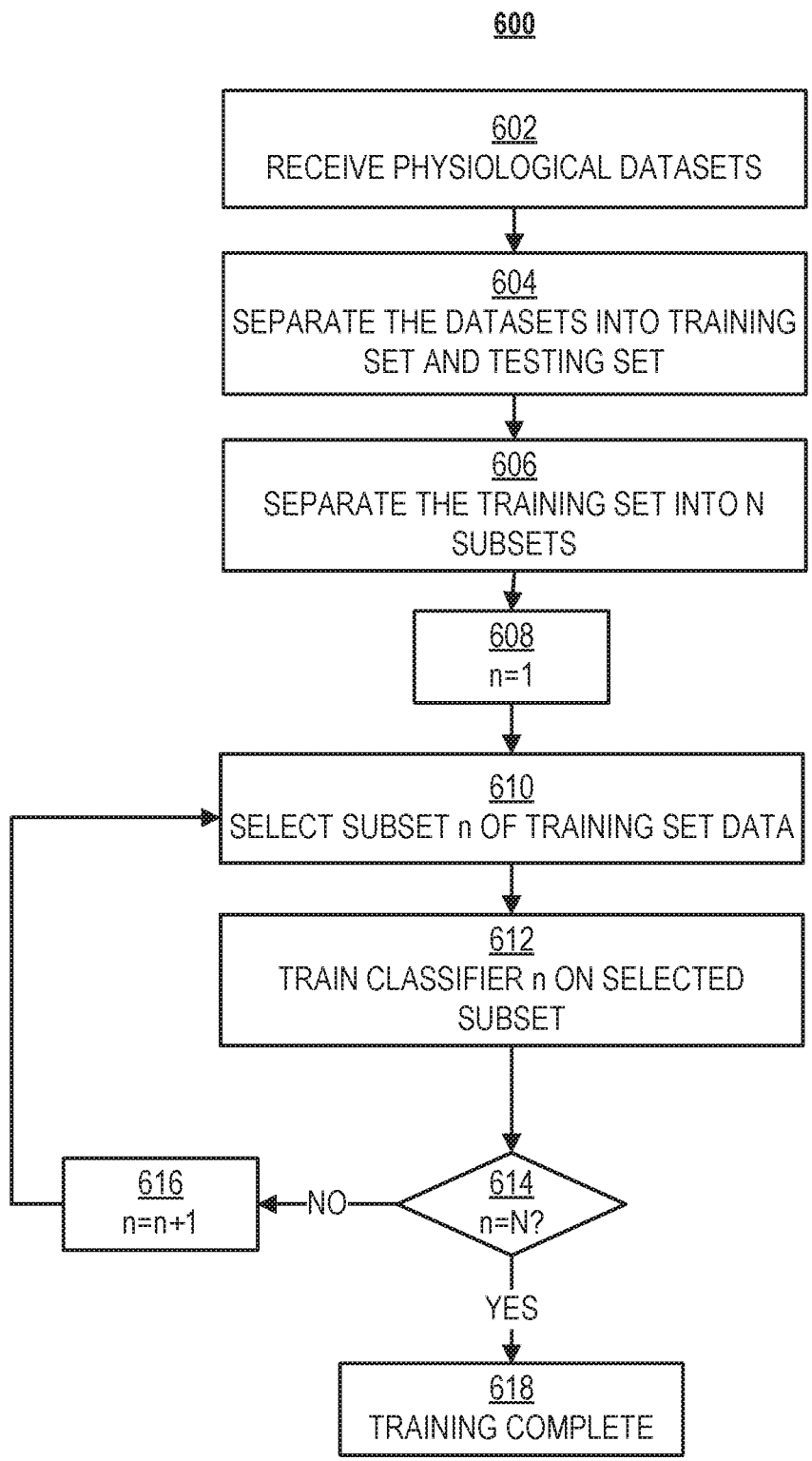
FIG. 6 is a flow diagram depicting a process, at the training stage, for training a set of classifiers on physiological data, according to an illustrative implementation of the disclosure.

FIG. 6 is a flow diagram depicting a process, at the training stage, for training a set of classifiers on physiological data, according to an illustrative implementation of the disclosure. The method 600 includes the steps of receiving physiological datasets (step 602), separating the dataset into a training set and a testing set (step 604), separating the training set into N subsets (step 606), and initializing an iteration parameter n to one (step 606). The n-th subset of the training set data is selected (step 610), and an n-th classifier is trained on the selected subset (step 612). Steps 610 and 612 are repeated until the desired number of classifiers (i.e., N), which may be configured by the user, have been trained.

At step 602, physiological datasets are received, for which agent exposure times are known. At step 604, the received datasets are separated into a training set and a testing set. The training set is used to develop the classifiers and is provided as input to the training stage 102. The testing set is used to assess the performance of the resulting classifiers and is provided as input to the testing stage 104. An example method of assessing the performance of the classifiers in the testing stage 104 is described in relation to FIG. 8.

At step 606, the received datasets are divided into N subsets, e.g. by subset selector 214. Each subset of the training data includes data recorded during specific time intervals, e.g. one time interval for each 12 hour period, 24 hour period, 36 hour period, or any other suitable time interval after agent exposure. At step 608, the iteration parameter n is initialized to one. The iteration parameter n is representative of a selected subset of the training set.

At step 610, the subset selector 214 selects an n-th subset of the training set data. Optionally, the training set data may be processed by the preprocessor 216 (e.g., to get the training set data into a suitable form). These processes are described in more detail in relation to FIG. 3.

At step 612, the n-th classifier is trained on the corresponding subset. In some implementations, there is one classifier trained for each day, 12 hour period, 36 hour period, or 48 hour period of data recorded after the patient was exposed to an agent as well as a baseline classifier that characterizes pre-exposure somatic function. In some implementations, the classifiers are random forest classifiers, each of which uses a set of decision trees to generate a final classification decision.

At decision block 614, it is determined whether the iteration parameter n equals the desired total number of subsets N. In an exemplary implementation, N is set to 7, and there are seven classifiers each trained on a respective day of a week of post exposure data. In an example, the total number of subsets N may be set to a larger number (such as 10, 25, 50, 100, for example), and the results may be analyzed until a plateau in performance is reached. Using a larger value for N generally involves more computation, so it may be desirable to set N to a value that is large enough to achieve a desired performance but small enough to be computationally efficient. In one example, N may be set to 50 in order to achieve a plateau in performance while being computationally efficient. If n does not equal N, the iteration parameter n is incremented at step 616 and the process 600 returns to step 610 to select the next subset of training set data. When iteration parameter n has reached its final value N, training is complete at step 618. In particular, as a result of the training, N classifiers have been generated. The classifiers may be different because they were tuned for optimal performance on different subsets of the training set records, though each classifier resulted from the same mathematical or computational structure.

In some implementations, the number of classifiers N used is three: one baseline pre-exposure classifier that is trained on pre-exposure data obtained from the same patient or a population of patients, one post-exposure and pre-symptomatic classifier that is trained on data that was recorded after exposure to an agent but before the patient exhibited symptoms of infection or intoxication, and one post-exposure and post-symptomatic classifier that is trained on data that was recorded after exposure to the agent and after the patient began to exhibit symptoms of infection or intoxication. Rather than using a different classifier for each fixed post-exposure time interval, this method of using just three classifiers defined based on exposure time and time of symptom(s) arising may be advantageous because of its simplicity.

Figure 7:
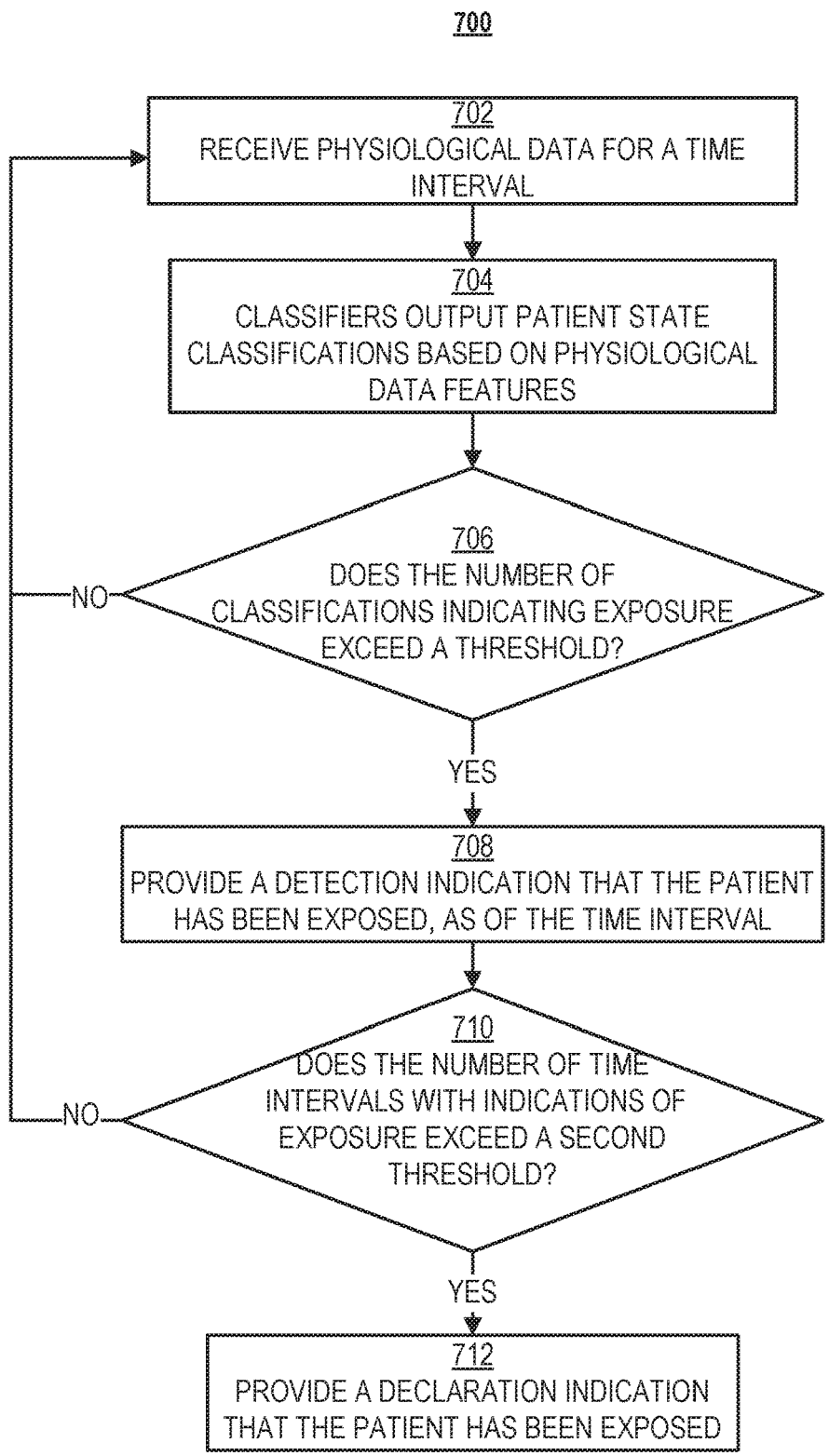
FIG. 7 is a flow diagram depicting a process, at the application stage, for testing and using classifiers to determine a physiological state classification associated with physiological data and to provide a declaration indication, according to an illustrative implementation of the disclosure.

FIG. 7 is a flow diagram depicting a process, at the application stage or testing stage, for testing and using classifiers to determine a physiological state classification associated with physiological data and to provide a declaration indication, according to an illustrative implementation of the disclosure. The method 700 includes the steps of receiving a physiological dataset for a time interval (step 702), using classifiers to output patient state classifications based on physiological data features (step 704), determining whether the number of classifications indicating exposure to an agent merits a detection indication (steps 706 and 708), and deciding whether the number of detection indications merits a declaration indication (steps 710 and 712). Steps 706 and 710 are repeated until step 712 when a declaration indication is provided indicating a prediction that the patient has been exposed to an agent.

At step 702, physiological data from a patient is received. The method 700 may be applied in relation to the testing stage 104, in which case the agent exposure time associated with the data is known. The method 700 may also be applied in relation to the application stage 106, in which case the agent exposure time associated with the physiological data is unknown. The physiological data may be preprocessed as discussed in relation to FIG. 4.

At step 704, a set of trained classifiers (e.g. those trained in relation to FIG. 6) provide patient state classifications based on the received physiological data. In some implementations, the classifiers are random forest classifiers that are trained on a respective post agent exposure time interval. The classifiers my give different levels of significance to different features of the physiological data, e.g. as is explained in relation to FIG. 9, which displays the types of physiological data sorted by the feature importance metric assigned by each daily classifier. The classifiers may each be configured to have a particular maximum probability of false alarm, e.g. as explained in relation to FIG. 10, by setting the threshold required for a classification indicating exposure. In some implementations, the threshold determines the number or proportion of decision trees in a random forest that are required to vote for a classification indicating exposure in order for the entire forest to output the classification. Thresholds may be set individually for each classifier. For each classifier, a probability of false alarm can be calculated by using baseline, pre-exposure physiological data to check for false positives for every threshold. The threshold can then be set sufficiently high to limit the probability of false alarm, such as to 5%. This is explained in more detail in relation to FIG. 10.

At decision block 706, it is determined, e.g. by classification collector 456, whether the number of classifications indicating exposure meets or exceeds a threshold. The threshold may be a threshold level of classifiers out of a total number of classifiers, such as 1 out of 6 classifiers, 2 out of 7 classifiers, or any suitable threshold level. If exposure is detected, then a detection indication is provided to indicate that the patient was likely exposed to the agent as of the time interval at step 708.

Figure 12:
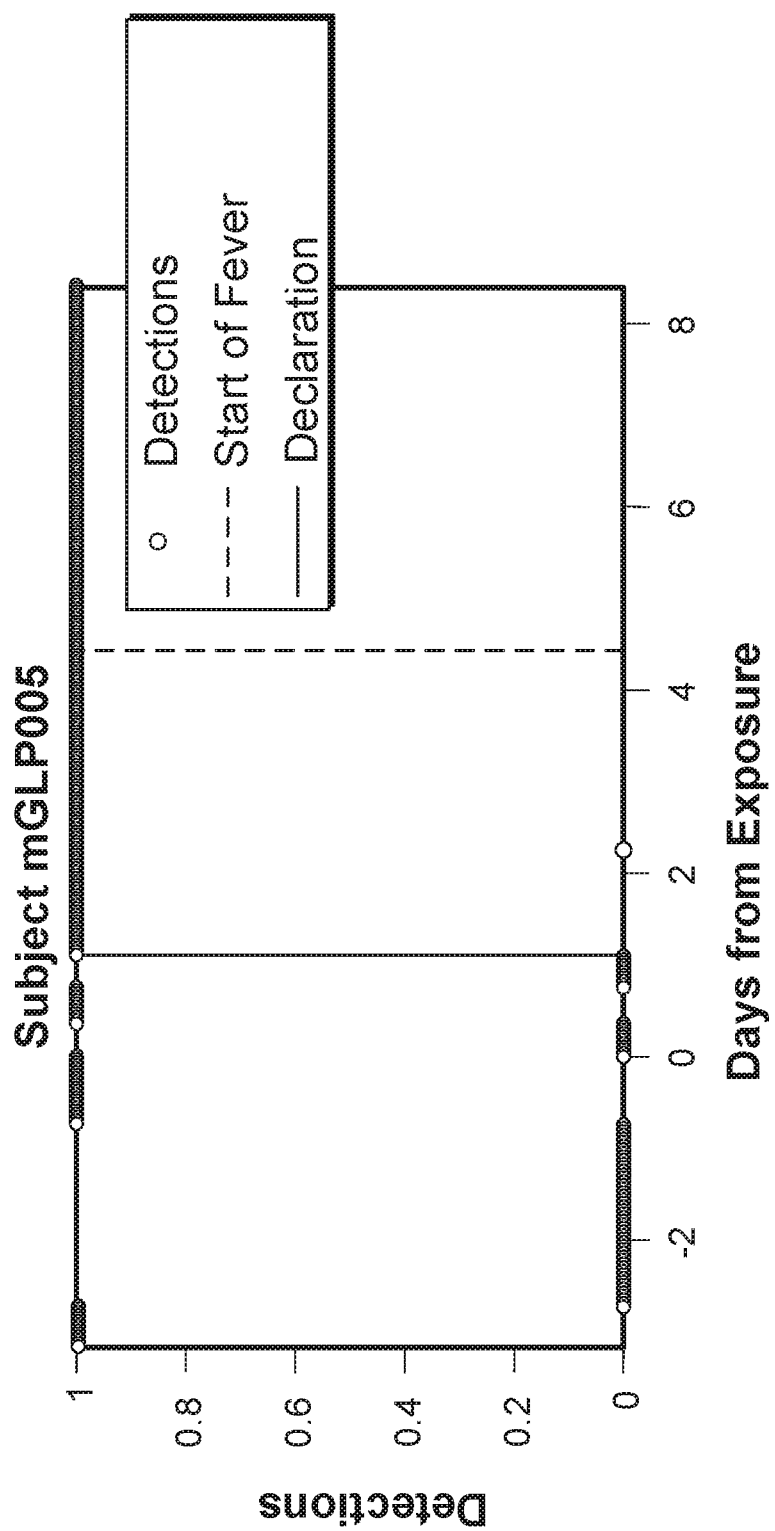
FIG. 12 is a chart of detection indications and a declaration indication compared to pathogen exposure and the start of febrile symptoms, according to an illustrative implementation of the disclosure.

At decision block 710, it is determined (e.g. by classification aggregator 458 or classification aggregator 336) whether the number of time intervals with detection indications exceeds a threshold. The threshold may represent a requisite number of detection indications or be represented as a requisite number of indications that must be present within a specified number of recent time intervals. When the threshold is exceeded, a declaration indication is provided at step 712 to indicate that the patient has been exposed to the agent. FIG. 12 shows exemplary detections and a declaration for an experimental subject.

Figure 8:
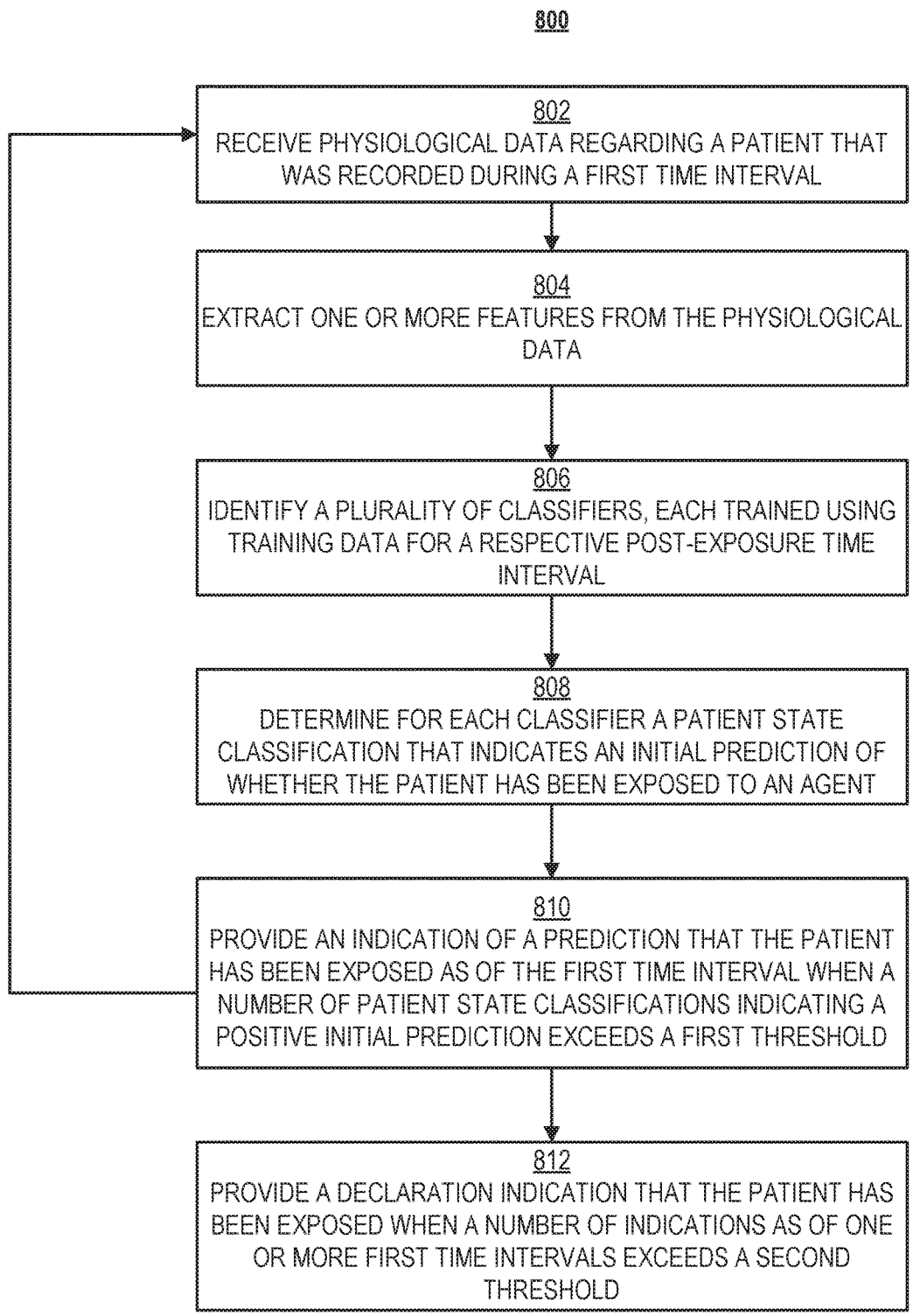
FIG. 8 is a flow diagram depicting a method for infection detection, according to a illustrative implementation of the disclosure.

FIG. 8 is a flow diagram depicting a method for predicting whether a patient has been exposed to an agent, according to an illustrative implementation of the disclosure. The method 800 includes the steps of receiving physiological data regarding a patient that was recorded during a first time interval (step 802), extracting one or more features from the physiological data (step 804), identifying a plurality of classifiers each trained using training data for a respective post-exposure time interval (step 806), determining for each classifier a patient state classification that indicates an initial prediction of whether the patient has been exposed to the agent (step 808), providing an indication of a prediction that the patient has been exposed as of the first time interval when a number of patient state classifications indicating a positive initial prediction that the patient has been exposed to the agent exceed a first threshold (step 810), and providing a declaration indication that the patient has been exposed when a number of indications from step 810 as of one or more first time intervals exceeds a second threshold.

At step 802, physiological data regarding a patient that was recorded during a first time interval. The physiological data is received (e.g. by receiver 452) and the method may be applied in relation to the application stage 106, in which case the agent exposure time associated with the physiological data is unknown. The physiological data may include pulmonary data, blood pressure data, electrocardiography data, and temperature data. In some implementations, the disclosure operates using only ECG data, which may be collected from wearable monitors and sparse. The physiological data may be preprocessed as discussed in relation to FIG. 4 at step 804 in order to make the physiological data suitable for classification and extract one or more features from the physiological data. Preprocessing may be carried out as described in relation to FIG. 4 (e.g. by preprocessor 454).

At step 806, a set of trained classifiers are identified (e.g. those trained in relation to FIG. 6) that are each trained using training data for a respective post-exposure time interval. In some implementations, the classifiers are random forest classifiers that are trained on a respective post agent exposure time interval of 24 hours. The classifiers my give different levels of significance to different features of the physiological data, e.g. as is explained in relation to FIG. 9, which displays the types of physiological data sorted by the feature importance metric assigned by each daily classifier. At least one classifier may be trained on baseline (pre-exposure) somatic data or known un-exposed data from other representative patients.

At step 808, each classifier determines a patient state classification that indicates a prediction of whether the patient has been exposed to an agent. The classifiers may each be configured to have a certain probability of false alarm, e.g. as explained in relation to FIG. 10, by changing the threshold required for a classification indicating exposure. In some implementations, the threshold determines the number or proportion of decision trees in a random forest that are required to vote for a classification indicating exposure in order for the entire forest to output the classification. Thresholds may be set individually for each classifier. For each classifier, a probability of false alarm can be calculated by using baseline, pre-exposure physiological data to check for false positives for every threshold. The threshold can then bet set sufficiently high to limit the probability of false alarm. Mean classifier scores are discussed in more detail in relation to FIG. 11.

At step 810, an indication that the patient has been exposed to the agent as of the first time interval is provided when a number of patient state classifications indicating a positive prediction that the patient has been exposed to the agent exceeds a first threshold (e.g. as determined by classification collector 456). The threshold may be a threshold level of classifiers out of a total number of classifiers, such as 1 out of 6 classifiers, 2 out of 7 classifiers, or any suitable threshold level. Detections are explained in greater detail with respect to FIGS. 4 and 12.

Steps 802 through 810 are repeated for one or more additional first time intervals, and, at step 812, a declaration indication that the patient has been exposed to the agent is provided when a number of indications from step 810 as of one or more first time intervals exceeds a second threshold (e.g. as determined by classification aggregator 458). The threshold may represent a requisite number of detection indications or be represented as a requisite number of indications that must be present within a specified number of recent time intervals, such as m detections within the last n intervals, where m and n are configurable integer parameters. FIG. 12 shows exemplary detections and a declaration for an experimental subject.

In an exemplary implementation, an experiment was performed involving non-human primate (NHP) subjects. The NHP subjects were exposed to either of two viral hemorrhagic fevers (Ebola and Marburg viruses) and monitored to collect high resolution physiological data. The primates were divided into three groups MARV IM, MARV aerosol, EBOV aerosol based on the virus and method of exposure, aerosol or intramuscular injection (IM). MARV IM primates received Marburg virus via intramuscular injection exposure. MARV aerosol primates received Marburg virus via aerosol exposure. EBOV aerosol primates received Ebola virus via aerosol exposure. Data were normalized to remove diurnal rhythms and shorten fluctuations, then provided to a supervised binary class (pre- and post-exposure) random forest machine learning algorithm. Random forests were chosen for their robustness against feature-rich and noisy data while minimizing over-fitting. A random forest was built every day post-exposure. Subjects were separated into training and testing sets, generally at a ratio of 2 training subjects for each testing subject, and every testing subject's data was provided to the model for an exposure prediction every 30 min. Using a thresholding method for minimizing false alarms (described in relation to FIG. 10), exposure declarations were found to range from 27 h (for Ebola) to 40 h (for Marburg) before the onset of fever (defined as a temperature 1.5° C. above a diurnal baseline sustained for two hours). The remaining FIGS. 9-12 display results from the experiment.

FIG. 9 is a table indicating the physiological data that are important to the patient state classification for the days after agent exposure. Since the classifiers used in the present disclosure are trained on distinct, respective post-exposure time intervals, each classifier may give a different feature importance metric to each feature of the physiological data. Feature importance may change for each category of physiological data, e.g. between ECG, pulmonary data, temperature data, and blood pressure data, and even between the summary statistics or other features computed for each category of physiological data. For example, mean heart rate and mean temperature may carry significantly more predictive importance than the standard deviation of heart rate or the lower quartile of blood pressure. The important features may depend on which post-exposure time interval is being considered, the route of exposure (in one example, when the route of exposure is aerosol, pulmonary data may be more predictive than other types of data), and the particular agent. The classifiers may further output a list of the features that indicates the respective feature importance metric for each feature, e.g. as shown in FIG. 9. The feature types listed in FIG. 9 are listed in decreasing order of importance, with features having more predictive importance being listed higher in the table. Feature types, rather than individual features, are listed for clarity since single features within a class were highly correlated. All subjects experienced the onset of febrile symptoms by day 5, which can be seen in FIG. 9 in the Day 5, Day 6, and Day 7 columns, which rank temperature as the most predictive feature. Day 4 gives some predictive weight to fever but it does not rank ahead of features used in pre-fever days (e.g. Days 2 and 3), which give more importance to more subtle biological signals, such as respiratory rate, blood pressure, and ECG features (such as QRS, QT, and PR intervals, heart rate). Moreover, features may be generated in a domain that is different from the time domain, such as the frequency (Fourier) or wavelet domains. The respective specific post-exposure time interval for a first classifier in the plurality of classifiers is approximately two days after exposure, and the first classifier uses pulmonary data, blood pressure data, and electrocardiography data. The respective specific post-exposure time interval for a second classifier in the plurality of classifiers is approximately three days after exposure, and the second classifier uses electrocardiography data and pulmonary data. The respective specific post-exposure time interval for a third classifier in the plurality of classifiers is approximately four days after exposure, and the first classifier uses electrocardiography data, blood pressure data, and temperature data. The respective specific post-exposure time interval for a fourth classifier in the plurality of classifiers is approximately five days after exposure, and the fourth classifier uses temperature data, electrocardiography data, and blood pressure data. The respective specific post-exposure time interval for a fifth classifier in the plurality of classifiers is approximately six days after exposure, and the fifth classifier uses temperature data, electrocardiography data, and pulmonary data.

Figure 10:
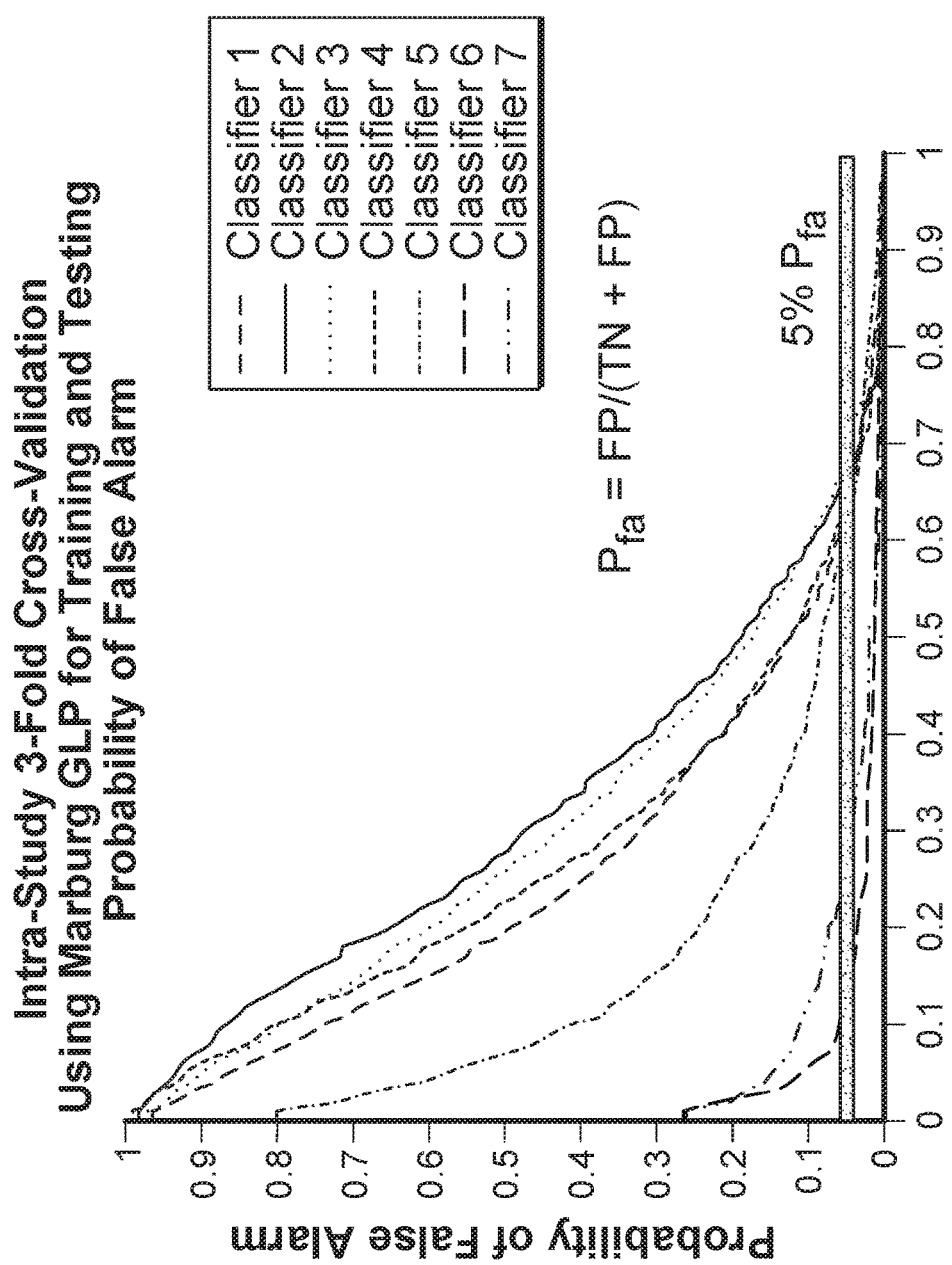
FIG. 10 is a chart displaying how a classification threshold for each classifier is set to provide a given probability of false alarm, according to an illustrative implementation of the disclosure.

FIG. 10 is a chart displaying how a classification threshold for each classifier is set to provide a given probability of false alarm, according to an illustrative implementation of the disclosure. For each classifier, a probability of false alarm can be calculated by using baseline, pre-exposure physiological data. Any classification indicating infection made based on pre-exposure data is a false alarm, which is also referred to as a false positive, and, by varying the threshold used in a random forest classifier, a chart of the probability of receiving a false alarm versus the threshold rate can be generated. The probability of false alarms is defined as the number of false positives divided by the sum of the number of true negatives and the number of false positives. This is shown in FIG. 10 as $P_{fa}$=FP/(TN+FP), which uses $P_{fa}$ for the probability of false alarms, FP to be the number of false positives, and TN to be the number of true negatives. In FIG. 10 it can be seen how a desired probability of false alarm corresponds to a score threshold for each classifier, as the horizontal line indicating a fixed probability of false alarm will intersect the probability curve for each classifier at the desired minimum threshold. Setting the classification threshold at, or above, the x-axis value of the intersection will yield a probability of false alarm that is less than or equal to the desired probability of false alarm (e.g., 5%). It will be apparent to one of ordinary skill in the art how such a plot may be used to determine the minimum threshold for each classifier to achieve a given probability of false alarm.

FIG. 10 generally shows that earlier classes generally require higher thresholds. The earlier classifiers are using physiological data that is more similar to the baseline data. Whereas, in the experiment, the day 4 through 7 classifiers could use fever as a predictive feature and consequently yielded ROC AUC values approaching one, indicating nearly perfect performance during febrile symptoms. This explains the overall trend observed from the data in FIG. 10 that classifiers from later days require a lower threshold to achieve a given probability of false alarm. The probability of false alarm analysis can be expanded beyond detection thresholding to evaluate model performance. The probability of detection can be defined as the ratio of the number of true positive indication to the number of all positive indications. The probability of detection and probability of false alarm can be used to generate a receiver operating characteristic (ROC) curve, that can be used to summarize the performance of the classifier by calculating an area under the curve. ROC curves describe the sensitivity and specificity of a test and can be summarized by the area under the curve, wherein an AUC of 1.0 refers to a perfectly sensitive and specific detector and a value of 0.5 indicates that the test cannot distinguish between classes better than a coin flip. The precision of the classifiers may also be calculated as the ratio of false positive indications to all (false and true) positive indications.

Figure 11:
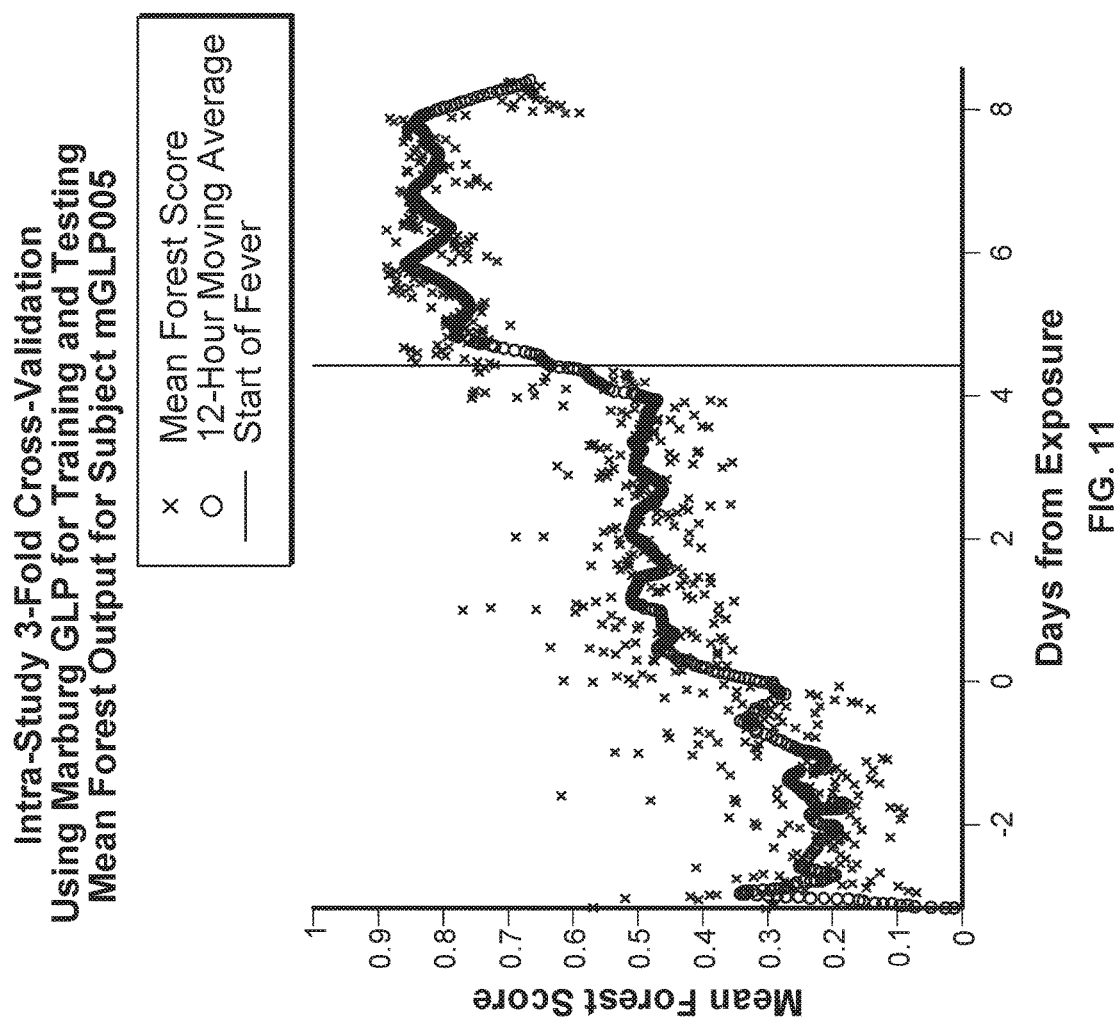
FIG. 11 is a chart of the classifier scores as a function of time from exposure to pathogen, according to an illustrative implementation of the disclosure.

FIG. 11 is a chart of the classifier scores as a function of time from exposure to an agent, according to an illustrative implementation of the disclosure. The x-axis of the graph is indicative of a number of days from a subject's exposure to an agent and ranges from three days prior to exposure to eight day post-exposure. The y-axis of the graph represents the mean of the scores output by the random forest classifiers. The graph indicates the start of fever with a solid vertical line at a little more than 4 days post-exposure. The x marks indicate the mean score of the forest classifiers for a given time from exposure, and the circles indicate the moving average of the means reported for the previous 12 hours. As is shown in FIG. 11, a pre-exposure baseline is established before zero days of exposure, when the classifiers provide scores ranging from around 0.1 to 0.4. In the days immediately following exposure but before the start of fever, the classifier scores rise to a level above this pre-exposure baseline, with scores ranging from 0.35 to 0.6 for days 1 to 4. The classifier scores also rise sharply around the start of fever to a level of 0.7 to 0.9 for days 5-8. This behavior can be explained by individual forest scores: during the incubation period, forests 1-4 output scores higher than the pre-exposure baseline, whereas forests 5-7 do not. Forests 1-4 are trained on data with subtle, subclinical changes from baseline which become more obvious and detectable after fever onset. After febrile symptoms forests 1-7 collectively report scores significantly above the baseline. The data shown in FIG. 11 indicates that the systems and methods described herein are sensitive to exposure and may indicate infection well before the onset of fever.

FIG. 12 is a chart of detection indications and a declaration indication compared to agent exposure and the start of febrile symptoms, according to an illustrative implementation of the disclosure. The y-axis indicates detections on a binary scale, where 1 represents an infection detection and 0 represents no infection detection. The x-axis represents a number of days from a subject's exposure to an agent and ranges from 3 days before exposure to 8 days after exposure. The chart indicates detection indications as individual circle marks. Approximately one day from exposure, the number of detections exceeds a threshold, indicating a declaration of infection, which is shown on the chart as a solid vertical line. In the experiment, an "m×n" threshold was applied, requiring n=10 of the previous m=24 intervals to have a positive detection. In general, other values for n and m may be used without departing from the scope of the present disclosure. The onset of fever is indicated using a dashed vertical line at shortly after 4 days post-exposure. The data shown in FIG. 12 indicate that the early warning time that the systems and methods of the present disclosure provide with respect to febrile symptoms in this example is approximately 3 days. In other similar experiments that were performed for different viruses, exposure declarations were found to range from 27 hours of early warning time for the Ebola virus and 40 hours of early warning time for the Marburg virus. The primates were divided into three groups MARV IM, MARV aerosol, and EBOV aerosol based on virus and exposure method, as explained above. The systems and methods of the present disclosure were applied using different combinations of groups for training and testing data. When the training set used MARV aerosol and the testing set used MARV aerosol, the disclosure provided 40.0 hours of early warning time, with a precision of 0.86 using n=10 and m=24. When the training set used MARV IM and the testing set used MARV IM, the disclosure provided 64.8 hours of early warning time, with a precision of 0.92 using n=6 and m=18. When the training set used EBOV aerosol and the testing set used EBOV aerosol, the disclosure provided 43.8 hours of early warning time, with a precision of 0.85 using n=6 and m=18. When the training set used MARV IM and the testing set used MARV aerosol, the disclosure provided 35.3 hours of early warning time, with a precision of 0.88 using n=10 and m=24. When the training set used EBOV aerosol and the testing set used MARV aerosol, the disclosure provided 21.5 hours of early warning time, with a precision of 0.90 using n=6 and m=18. When the training set used only the ECG data from MARV aerosol and the testing set used only the ECG data from MARV aerosol, the disclosure provided 56.0 hours of early warning time, with a precision of 0.80 using n=6 and m=18.

Implementing this type of early-warning system could save lives of health care workers, military service members, patients, and other susceptible individuals. During the 2014 West Africa Ebola outbreak, for instance, health care workers at higher risk of viral exposure could have been monitored persistently for the earliest possible indications of viral exposure. More commonly, patients in post-operative or critical care units could be monitored for infection and treated well before clinical symptoms, viremia/bacteremia, or septic shock. Higher specificity iterations of this approach and knowledge of the causative agent could inform very early therapeutic intervention without departing from the scope of the disclosure. Furthermore, using very feature sparse datasets, such as those that could be collected using wearable sensor platforms, would enable this technique to be implemented in, for example, rugged military environments.

While various embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

What is claimed is:

1. A method for predicting whether a patient has been exposed to a pathogen prior to onset of a clinical symptom, the method comprising:
    (a) receiving, by at least one processor, physiological data comprising electrocardiography data regarding the patient that was recorded during a first time interval after suspected exposure and prior to onset of the clinical symptom;
    (b) extracting, by the at least one processor, one or more features from the physiological data, wherein each feature is representative of the physiological data during the first time interval;
    (c) providing a plurality of classifiers, wherein each classifier is trained using training data for a respective specific post-exposure time interval, wherein each classifier is selected from the group consisting of a random forest classifier, a k-nearest neighbor classifier, and a nave Bayes classifier;
    (d) determining, by the at least one processor, for each classifier and based on a respective subset of the one or more features, a patient state classification that indicates an initial prediction of whether the patient has been exposed to the pathogen; and
    (e) providing an indication of a prediction that the patient has been exposed to the pathogen when a number of patient state classifications indicating a positive initial prediction that the patient has been exposed to the pathogen exceeds a first threshold.

2. The method of claim 1, further comprising:
    repeating (a)-(e) for one or more additional first time intervals; and
    providing an indication that the patient has been exposed to the pathogen when a number of indications that the patient has been exposed to the pathogen exceeds a second threshold.

3. The method of claim 1, wherein the pathogen is selected from the group consisting of a viral pathogen and a bacterial pathogen.

4. The method of claim 1, further comprising:
    (f) treating the subject for infection by the pathogen prior to onset of the clinical symptom when the indication of the prediction that the patient has been exposed to the pathogen is provided.

5. The method of claim 1, wherein the clinical symptom is fever.

6. The method of claim 1, wherein the pathogen is a viral pathogen.

7. The method of claim 1, further comprising performing electrocardiography on the patient to generate the electrocardiography data.

8. A system for predicting whether a patient has been exposed to a pathogen, the system comprising:
    at least one processor programmed to:
    (a) receive physiological data comprising electrocardiography data regarding the patient that was recorded during a first time interval after suspected exposure and prior to onset of the clinical symptom;
    (b) extract one or more features from the physiological data, wherein each feature is representative of the physiological data during the first time interval;
    (c) provide a plurality of classifiers, wherein each classifier is trained using training data for a respective specific post-exposure time interval, wherein each classifier is selected from the group consisting of a random forest classifier, a k-nearest neighbor classifier, and a nave Bayes classifier;
    (d) determine, for each classifier and based on a respective subset of the one or more features, a patient state classification that indicates an initial prediction of whether the patient has been exposed to the pathogen; and
    (e) provide an indication of a prediction that the patient has been exposed to the pathogen when a number of patient state classifications indicating a positive initial prediction that the patient has been exposed to the pathogen exceeds a first threshold.

9. The system of claim 8, wherein the at least one processor is further programmed to:
    repeating (a)-(e) for one or more additional first time intervals; and
    providing an indication that the patient has been exposed to the pathogen when a number of indications that the patient has been exposed to the pathogen exceeds a second threshold.

10. The system of claim 8, wherein the agent is selected from the group consisting of a viral pathogen and a bacterial pathogen.

11. The system of claim 8, wherein at least one classifier is trained on training physiological data obtained after known exposure to the pathogen and prior to onset of the clinical symptom and wherein at least one classifier is trained on physiological data obtained after known exposure to the pathogen and after onset of the clinical symptom.

12. A method for determining the likelihood of exposure to a pathogen, the method comprising:
    (a) receiving electrocardiography data obtained during a first time interval from a subject suspected of being exposed to the pathogen prior to onset of a clinical symptom;
    (b) extracting, by at least one processor, one or more features from the electrocardiography data;
    (c) providing a plurality of classifiers, wherein each classifier is configured to select an exposure state associated with physiological data from the subject, wherein each classifier is selected from the group consisting of a random forest classifier, a k-nearest neighbor classifier, and a naïve Bayes classifier, wherein the physiological data comprises the electrocardiography data, and wherein the exposure state indicates whether the subject has been exposed to the pathogen;

(d) aggregating, by the at least one processor, the exposure states from the classifiers to determine a number of exposure states that indicate that the subject has been exposed to the pathogen to determine the likelihood of exposure; and (e) treating the subject for infection by the pathogen prior to onset of the clinical symptom when a likelihood of exposure is greater than a threshold value.

13. The method of claim 12, wherein the clinical symptom is fever.

* * * * *

UNITED STATES PATENT AND TRADEMARK OFFICE
CERTIFICATE OF CORRECTION

PATENT NO. : 10,332,638 B2
APPLICATION NO. : 15/212769
DATED : June 25, 2019
INVENTOR(S) : Albert Joseph Swiston et al.

Page 1 of 1

It is certified that error appears in the above-identified patent and that said Letters Patent is hereby corrected as shown below:

In the Claims

Column 21, Line 42, the word "nave" should read -- naïve --

Column 22, Line 23, the word "nave" should read -- naïve --

Signed and Sealed this
Third Day of September, 2019

Andrei Iancu
*Director of the United States Patent and Trademark Office*